(12) United States Patent
Sakuta

(10) Patent No.: US 7,713,520 B2
(45) Date of Patent: May 11, 2010

(54) COSMETIC COMPRISING A SILICONE POLYMER

(75) Inventor: Koji Sakuta, Annaka (JP)

(73) Assignees: Shin-Etsu Chemical Co., Ltd., Tokyo (JP); NOF Corporation, Tokyo (JP)

( * ) Notice: Subject to any disclaimer, the term of this patent is extended or adjusted under 35 U.S.C. 154(b) by 459 days.

(21) Appl. No.: 10/594,734

(22) PCT Filed: Mar. 31, 2005

(86) PCT No.: PCT/JP2005/006306

§ 371 (c)(1), (2), (4) Date: Sep. 29, 2006

(87) PCT Pub. No.: WO2005/094758

PCT Pub. Date: Oct. 13, 2005

(65) Prior Publication Data

US 2007/0196291 A1 Aug. 23, 2007

(30) Foreign Application Priority Data

Mar. 31, 2004 (JP) ............... 2004-102684

(51) Int. Cl.
A61Q 5/12 (2006.01)
(52) U.S. Cl. .................................. 424/70.12
(58) Field of Classification Search ............ 424/78.08, 424/70.122, 70.12
See application file for complete search history.

(56) References Cited

U.S. PATENT DOCUMENTS

| 5,237,035 | A | 8/1993 | O'Lenick, Jr. et al. |
| 5,468,475 | A | 11/1995 | Shaku et al. |
| 5,648,422 | A | 7/1997 | Bowers et al. |
| 5,648,442 | A | 7/1997 | Bowers et al. |
| 6,225,431 | B1 * | 5/2001 | Bowers et al. ............... 526/287 |
| 6,673,883 | B1 | 1/2004 | Rowan |

FOREIGN PATENT DOCUMENTS

| EP | 0292760 A2 | 11/1988 |
| JP | 63-277246 A | 11/1988 |
| JP | 5-70321 A | 3/1993 |
| JP | 6-135816 A | 5/1994 |
| JP | 6-15270 A | 6/1994 |
| JP | 6-157269 A | 6/1994 |
| JP | 6-157270 A | 6/1994 |
| JP | 6-157271 A | 6/1994 |
| JP | 7-51355 A | 2/1995 |
| JP | 7-502053 | 3/1995 |
| JP | 7-118123 A | 5/1995 |
| JP | 2533772 B2 | 6/1996 |
| JP | 9-48855 A | 2/1997 |
| JP | 9-183819 A | 7/1997 |
| JP | 9-296019 A | 11/1997 |
| JP | 2000-212376 A | 6/2000 |
| JP | 2000-212376 A | 8/2000 |
| JP | 2001-508480 | 6/2001 |
| JP | 2002-80402 A | 3/2002 |
| JP | 2003-40842 A | 2/2003 |
| JP | 2003-40942 A | 2/2003 |
| WO | WO-96/32436 A1 | 10/1996 |

OTHER PUBLICATIONS

Polymer Structure, 2003, URL <http://plc.cwru.edu>.*

* cited by examiner

Primary Examiner—Johann R Richter
Assistant Examiner—Danielle Sullivan
(74) Attorney, Agent, or Firm—Birch, Stewart, Kolasch & Birch, LLP

(57) ABSTRACT

A cosmetic comprising (A) a polymer having repeating units represented by the following formula (I) and repeating units represented by the following formula (II)

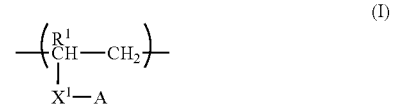

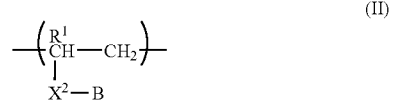

wherein each $R^1$ may be the same with or different from each other and is a hydrogen atom or a methyl group,
each of $X^1$ and $X^2$ is a divalent aromatic group having 2 to 10 carbon atoms or a group represented by the formula, $-COOR^7-$, wherein $R^7$ is an aliphatic-group bonded to A or B,
A is an organopolysiloxane residue, and
B is a group represented by the following formula (1),

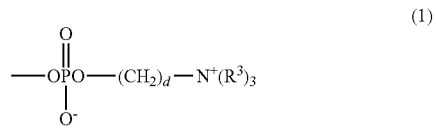

wherein each $R^3$ may be the same or different from each other and is an alkyl group having 1 to 20 carbon atoms and d is an integer of from 1 to 10.

35 Claims, No Drawings

COSMETIC COMPRISING A SILICONE POLYMER

This application is the U.S. National Stage entry of PCT/JP2005/006306, filed Mar. 31, 2005, and for which priority is claimed under 35 U.S.C. §120. This application also claims priority under 35 U.S.C. §119(a) on Patent Application No. 2004-102684 filed in Japan on Mar. 31, 2004. The entire contents of each application is hereby incorporated by reference.

FIELD OF THE INVENTION

The present invention relates to a cosmetic comprising a silicone polymer, specifically to a cosmetic comprising a highly biocompatible polymer having silicone residues and phosphoryl compounds residues.

PRIOR ART

A silicone polymer have been widely used for skincare cosmetics because it has little stickiness; spreads smoothly on the skin; gives refreshed feel to the skin; has a strong water repellency; and is highly safe to the skin. A silicone having a high molecular weight used for hair care products improves gloss of the hair and easiness to comb by forming a flexible film on the hair. It also has an excellent conditioning effect, too. Further, a film-forming silicone polymer is used to prevent makeup runs by sweat or the like. Examples of such polymer include solid trimethylsilylsilicate and silicone grafted acrylic copolymer. These polymers improve durability of a cosmetic film more than other oily films.

It is desired to improve adhesion to the skin or hair of these silicone polymers. One of the methods to improve the adhesion is concomitant use of a highly viscous oil or amino-modified oil. However, the highly viscous oil will spoil the touch, causing increase in stickiness and decrease of fresh feel. The amino-modified oil, when used in skincare products, may irritate the skin.

Another method to improve the adhesion is to introduce hydrophilic groups in the polymer. One example of such group is the one derived from phospholipid. It is known that the phospholipid is strongly hydrophilic and cosmetics comprising the phospholipid have moisturizing effect. An acrylic polymer grafted with phospholipid derivatives is known to form a film to protect the skin or hair and uses of the polymers for cosmetics are disclosed in, for example, Japanese Patent Application Laid-Open No. 5-70321, Japanese Patent Application Laid-Open No. 6-157269, Japanese Patent Application Laid-Open No. 6-157270, Japanese Patent Application Laid-Open No. 6-157271, and Japanese Patent No. 3178950, in which the polymers are obtained by copolymerizing radically reactive phospholipid monomers, hydrophobic monomers and hydrophilic monomers. However, these polymers have poor compatibility with silicone oils and do not improve smoothness to the touch, easiness to comb, and shiny appearance satisfactorily.

To make a polymer compatible with silicone oils, there is a method to provide the polymer with an organopolysiloxane moiety. Phospholipid-modified silicone polymers are known, for example, an organopolysiloxane polymer having phospholipid groups grafted to the organopolysiloxane main chain prepared by subjecting methylhydrogenpolysiloxane and a phospholipid derivative which has an aliphatic unsaturated group at an end to an addition-reaction as described in Japanese Patent NO. 2533772, a block polymer composed of siloxane units and phospholipid units prepared by polymerizing radically polymerizable phospholipid monomers using azo-type polymerization initiator having organopolysiloxane groups described in Japanese Patent Application Laid-Open No. 9-296019.

However, these polymers do not adhere to the skin or hair satisfactorily. Particularly, the polymer disclosed in Japanese Patent Application Laid-Open No. 9-296019 cannot have a higher molecular weight due to a larger amount of polymerization initiator in order to obtain a copolymer comprising a larger amount of the organopolysiloxane moieties. A film formed by the polymer is not strong enough to protect the skin or hair.

Copolymers of radically reactive phospholipid monomer with a silane or a siloxane is also known from Japanese Patent Application Laid-Open No. 7-51355, Japanese Patent Application Laid-Open No. 9-183819, Japanese Patent Application Laid-Open No. 2000-212376, published Japanese translation of PCT No. 2001-508480, and Japanese Patent Application Laid-Open No. 2002-80402.

However, these copolymers have hydrolizable alkoxy groups, which are undesirable for cosmetics because they cause change in cosmetic quality with time or form irritants to the skin. For example, a methoxy group is hydrolyzed to form methanol, which is undesirable to be present in cosmetic from the safety viewpoint. An ethoxy group is hydrolyzed to form ethanol, which is undesirable for cosmetic user who are sensitive to irritation caused by alcohols.

Meanwhile, a copolymer composed of an acrylic main chain and phospholipid grafts and siloxane grafts is disclosed in the published Japanese translation of PCT No. 7-502053. The copolymer is used to coat a surface of an instrument used in vivo. The disclosure teaches that, when the surface of the instrument is hydrophilic, a siloxane having reactive groups is used to subject the groups to a reaction with the surface. As an example of such a reactive group, a halogen atom is described. However, halogen is not desirable for applying to the skin, because the group such as Si—Cl is hydrolyzed to from hydrochloric acid.

Problems to be Solved by the Invention

The purpose of the present invention is to provide a cosmetic comprising a silicone polymer that adheres well to the skin or hair and is nonirritating.

Means to Solve the Problems

Thus, the present invention is:

(1) A cosmetic comprising (A) a polymer having repeating units represented by the following formula (I) and repeating units represented by the following formula (II)

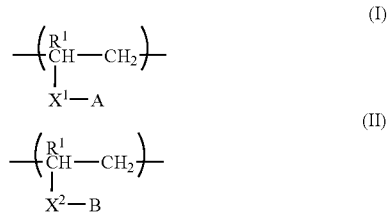

wherein each $R^1$ may be the same with or different from each other and is a hydrogen atom or a methyl group, each of $X^1$ and $X^2$ has 2 to 10 carbon atoms and is a divalent aromatic group or a group represented by the formula, —COOR$^7$—, wherein R$^7$ is an aliphatic group bonded to A or B, A is an organopolysiloxane residue, and B is a group represented by the following formula (1),

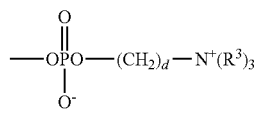

(1)

wherein each $R^3$ may be the same or different from each other and is an alkyl group having 1 to 20 carbon atoms and d is an integer of from 1 to 10.

Preferred embodiments of the aforesaid invention are as follows:

(2) The cosmetic according to (1) above, wherein, in the repeating unit represented by the formula (I), $X^1$ is represented by the formula, —COO(CH$_2$)$_a$—, wherein a is an integer of from 1 to 9, or a phenylene group, and the organopolysiloxane residue A is represented by the following formula (2),

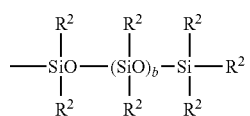

(2)

wherein b is an integer of from 1 to 300, and $R^2$ may be the same with or different from each other and is a $C_{1-30}$ alkyl or an aryl group, which is fluorinated or not substituted.

(3) The cosmetic according to (1) or (2), wherein, in the repeating unit represented by the formula (II), $X^2$ is represented by the formula, —COO(CH$_2$)$_c$—, wherein c is an integer of from 1 to 10, and $R^3$ is a methyl group.

(4) The cosmetic according to any one of (1) to (3), wherein the polymer further has repeating units (III) derived from at least one radically polymerizable monomer selected from the group consisting of unsaturated carboxylic acids and derivatives thereof, vinylpyrrolidone and derivatives thereof and styrene and derivatives thereof.

(5) The cosmetic according to (4), wherein the repeating unit (III) is derived from at least one selected from the group consisting of (meth)acylic acid, (meth)acrylates, (meth)acrylamides and vinylpyrrolidone.

(6) The cosmetic according to (5), wherein the (meth)acrylate is polyoxyalkylene mono(meth)acrylate, or (poly)glycerin mono(meth)acrylate.

(7) The cosmetic according to (6), wherein the polyoxyalkylene mono(meth)acrylate is represented by the following formula (3),

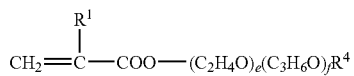

(3)

wherein $R^1$ is a hydrogen atom or a methyl group, $R^4$ is a hydrogen atom, a $C_{1-30}$ alkyl or acetyl group, and each of e and f is an integer of from 0 to 100 with a sum of e and f ranging from 5 to 200.

(8) The cosmetic according to (6), wherein the (poly)glycerin mono(meth)acrylate is represented by the following formula (4),

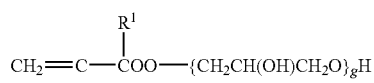

(4)

wherein $R^1$ is a hydrogen atom or a methyl group, and g is an integer ranging from 1 to 3.

(9) The cosmetic according to any one of (1) to (3), wherein the polymer comprises 1.0 to 29.0 mass % of the repeating unit (I) and 71.0 to 99.0 mass % of the repeating unit (II), based on a mass of the polymer.

(10) The cosmetic according to any one of (1) to (3), wherein the polymer comprises 30.0 to 99.5 mass % of the repeating unit (I) and 0.5 to 70.0 mass % of the repeating unit (II), based on a mass of the polymer.

(11) The cosmetic according to any one of (4) to (8), wherein the polymer comprises 1.0 to 29.0 mass % of the repeating unit (I), 0.5 to 69.5 mass % of the repeating unit (II), and 29.5 to 98.5 mass % of the repeating unit (III), based on a mass of the polymer (A).

(12) The cosmetic according to any one of (4) to (8), wherein the polymer comprises 30.0 to 99.0 mass % of the repeating unit (I), 0.5 to 69.5 mass % of the repeating unit (II), and 0.5 to 69.5 mass % of the repeating unit (III), based on a mass of the polymer (A).

In addition, the present inventions are cosmetics comprising various components used in cosmetics such as (B) an unctuous agent and (C) a $C_{2-10}$ compound having an alcoholic hydroxyl group.

Effects of the Invention

The silicone polymer in the present invention is nonirritating and improves a cosmetic in adhesion to the skin or hair. The polymer can be in a desired form, for example, a liquid of low or high viscosity, and a solid, by controlling a ratio of the repeating units or a degree of polymerization. Hydrophile-lipophile balance of the polymer can also be controlled. Therefore, it can be incorporated in a cosmetic as a various components such as an unctuous agent, a film-forming agent, an emulsifier, a powder treatment agent, a conditioning agent, and a moisturizing agent.

PREFERRED EMBODIMENTS OF THE INVENTION

The polymer (A) in the present invention has the following repeating units.

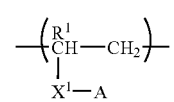

(I)

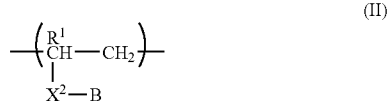

In the each repeating unit (I) and (II), each $R^1$ is a hydrogen atom or a methyl group, preferably a methyl group. A plurality of $R^1$, in the polymer may be the same with or different from each other.

Each of $X^1$ and $X^2$ has 2 to 10, preferably 3 to 8, carbon atoms, and is a divalent aromatic group or a group represented by the formula, —COOR$^7$—. In the group, —COOR$^7$—, $R^7$ is an aliphatic group bonded to A or B, and the carbonyl group thereof is bonded to a carbon atom in a main chain of the polymer. The group, $R^7$, may be represented by the formula, —(CH$_2$)$_a$—, wherein a is an integer of from 1 to 9, preferably from 2 to 7. Examples of the divalent aromatic group include phenylene, tolylene, xylylene, and mesitylene group, among which phenylene group is preferred.

In the repeating unit (I), A is an organopolysiloxane residue, preferably, a group represented by the following formula (2).

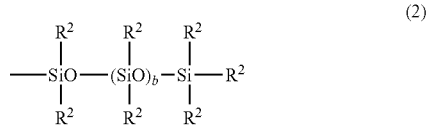

In the formula (2), b is an integer ranging from 1 to 300, preferably from 10 to 280, more preferably from 50 to 250. A polymer having a larger b than the aforesaid higher limit may have a lower adhesion or, when contained in a cosmetic comprising a hydrocarbon unctuous agent, a poorer compatibility with the unctuous agent. On the other hand, a polymer having a smaller b than the aforesaid lower limit may have lower smoothness or larger stickiness. Each $R^2$ is an alkyl or an aryl group, which is fluorinated or not substituted, having 1 to 30 carbon atoms. A plurality of $R^2$, in the polymer may be the same with or different from each other. Preferably, $R^2$ is a methyl, phenyl or trifluoro propyl group because a polymer having such $R^2$ hardly irritates the skin and is smooth to the touch.

In the repeating unit (II), B is a group represented by the following formula (1),

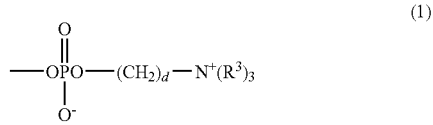

wherein each $R^3$ which may be different from each other, is an alkyl group having 1 to 20 carbon atoms. Preferably, $R^3$ is an alkyl group having 1 to 10 carbon atoms, more preferably a methyl group from a viewpoint of good adhesion to the skin. An integer, d, ranges from 1 to 10, preferably from 2 to 4.

The polymer (A) in the present invention may further have the repeating units (III), in addition to the aforesaid repeating units. The repeating unit (III) is derived from at least one radically polymerizable monomer selected from the group consisting of unsaturated carboxylic acids and derivatives thereof, vinylpyrrolidone and derivatives thereof and styrene and derivatives thereof.

Examples of the unsaturated carboxylic acid monomers and their derivative monomers include nonionic, anionic, cationic and amphoteric monomers. Examples of the nonionic monomers include alkyl (meth)acrylate such as methyl (meth)acrylate, ethyl (meth)acrylate, butyl (meth)acrylate, cyclohexyl (meth)acrylate, n-octyl (meth)acrylate, 2-ethylhexyl (meth)acrylate, lauryl (meth)acrylate, n-stearyl (meth)acrylate, isostearyl (meth)acrylate, behenyl (meth)acrylate, butoxy (meth)acrylate, benzyl (meth)acrylate, tetrahydrofurfuryl (meth)acrylate, and hydroxyetyl(meth)acrylate; polyoxyalkylene mono(meth)acrylate; (poly)glycerin (meth)acrylate; acrylamide and a monomer derived by a reaction of N-polyalkyleneoxy(meth)acrylamide with an alkylene oxide having 2 to 4 carbon atoms.

Examples of the cationic monomers include compounds derived by a reaction of (meth)acrylic acid with a quaternary ammonium salt of trialkylamine with epihalohydrin such as (meth)acryloyloxyhydorxypropyltrimethylammmonium chloride and (meth)acryloyloxyhydorxypropyltriethylammmonium chloride; amine derivative of (meth)acrylic acid or (meth)acrylamide such as dimethylaminoethyl (meth)acrylate, diethylaminoethyl (meth)acrylate, dimethylaminopropyl (meth)acrylate, a compound derived by a reaction of dimethylaminopropyl (meth)acrylamide with alkylalkanolamine having 1 to 4 carbon atoms; amine derivative of the aforesaid (meth)acrylic acids; and derivatives from (meth)acrylamide amine derivative such as (1) neutralized products with hydrochloric acid or lactic acid, (2) modified products with halogenated alkyl, for example, methyl chloride, ethyl chloride, methyl bromide or ethyl bromide, (3) modified products with halogenated fatty acid ester, for example, monochloroacetic acid or monochloropropionic acid, and (4) modified products with dialkyl sulfate ester, for example, dimethyl sulfate and diethyl sulfate.

Examples of the anionic monomers include (1) unsaturated carboxylic acids such as (meth)acrylic acid, maleic acid, maleic acid anhydride, itaconic acid, fumaric acid, and crotonic acid, (2) hafl esters of an unsaturated polybasic acid anhydride, for example, succinic acid anhydride and phthalic acid anhydride, with a (meth)acrylated having a hydroxy group, for example, hydroxy (meth)acrylate and hydroxypropyl (meth)acrylated, (3) monomers having a sulfonic acid group such as sulfoethyl (meth)acrylate, and (4) monomers having a phosphric acid group such as 2-(meth)acryloyloxyethyl acid phosphaste, 2-(meth)acryloyloxypropyl acid phosphaste, and 3-chloro-2-acid phosphoxypropyl (meth)acrylate.

Examples of the amphoteric monomers include amine derivatives of the aforesaid (meth)acrylic acid and amine derivatives of the aforesaid (meth)acrylamide such as dimethylaminoethyl (meth)acrylate and dimethylaminopropyl (meth)acrylamide; and a salt of monochloroacetic acid with aminopropanol. Other examples of the amphoteric monomers are triethanolamine salt of monochloroacetic acid, potassium salt of monochloroacetic acid, and modified sodium salt of monobromopropionic acid with halogenated fatty acid salts or propane sultone.

An example of the vinylpyrrolidone and derivatives thereof is N-vinylpyrrolidone and an example of the styrene and derivative thereof is methylstyrene.

Among the aforesaid various monomers, at least one monomer selected from the group consisting of (meth)acrylic acid, (meth)acrylic acid esters, polyoxyalkylene mono(meth)

acrylate, grycerin mono(meth)acrylate, polygrycerin mono(meth)acrylate, (meth)acrylamide and N-vinylpyrrolidone is preferably used.

More preferred reactive monomers are polyoxyalkylene mono(meth)acrylate represented by the following formula (3):

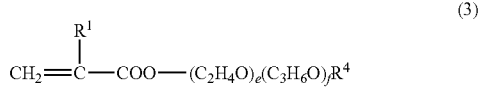

wherein $R^1$ is a hydrogen atom or a methyl group, $R^4$ is a hydrogen atom, a $C_{1-30}$ alkyl or acetyl group, and each of e and f is an integer ranging from 0 to 100 with a sum of e and f ranging from 5 to 200; and polygrycerin mono(meth)acrylate represented by the following formula (4):

wherein $R^1$ is a hydrogen atom or a methyl group, and g is an integer ranging from 1 to 3.

These monomers do not irritate the skin or mucous membranes. Therefore, a silicone polymer produced from the monomers can be used for cosmetics, even if the monomers remain unreacted in the silicone polymer.

The polymer (A) can be prepared by subjecting monomers for respective repeating units to an addition-reaction in the presence of an initiator for radical polymerization such as benzoyl peroxide, lauloyl peroxide, and azobisisobutyronitrile.

Examples of the monomers for preparing the repeating unit (I) are those represented by the following formulae (5) and (6).

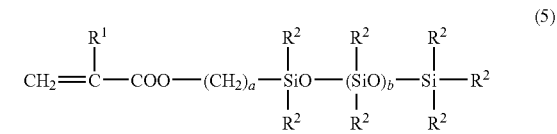

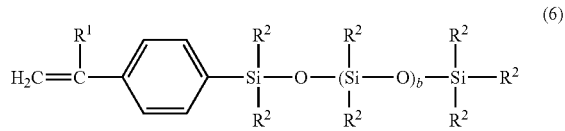

An example of the monomer for preparing the repeating unit (II) is the one represented by the following formula (7).

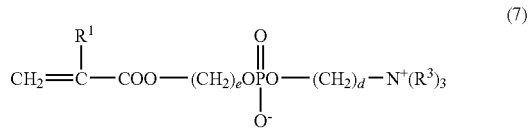

In these monomers, $R^1$, $R^2$ and $R^3$ are as defined above.

The repeating unit (III) may be derived from the monomers which have been described above.

If necessary, the polymerization may be carried out in an organic solvent. Examples of the solvent include aliphatic organic solvents such as pentane, hexane, decane, hexadecane, and octadecane; aromatic organic solvents such as benzene, toluene, and xylene; an alcoholic organic solvent such as methanol, ethanol, propanol, butanol, hexanol, and decanol; halogenized organic solvents such as chloroform, and carbon tetrachloride; and ketone type organic solvents such as acetone and methyl ethyl ketone. Preferably, the polymerization is carried out methanol or 2-propanol, more preferably, without solvent, because the polymer (A) is used for cosmetics.

The polymer in the present invention can be used for various cosmetics. Particularly, the polymer is suitable for cosmetics applied to the skin or hair. Examples of the cosmetics include skincare cosmetics such as milky lotions, cream, cleansing, facial pack formulas, oil liquid, massage cream, essence lotion, facial washes, deodorants, hand cream, and lip cream; makeup products such as makeup base, makeup powder, liquid foundation, oily foundation, cheek colors, eyeshadow, eyeliner, eyebrow, and lipsticks; hair care products such as shampoos, rinses, treatment and hair-setting agents; antiperspirants; UV-ray protective cosmetics such as sunscreen lotions and sunscreen cream.

The polymer may be incorporated in the cosmetic in an amount determined according to the type of the cosmetic. A content of the polymer can range from 0.5 to 99.0 mass %, depending on the form of the cosmetic, and preferably from 1.0 to 50 mass %, based on a total mass of the cosmetic.

The present cosmetic can incorporate, in addition to the aforesaid polymer (A), various components used for cosmetics such as (B) an unctuous agents and (C) $C_{2-10}$ compounds having an alcoholic hydroxyl group. These components will be explained below.

As the unctuous agent (B), use may be made of unctuous agent which is commonly used for cosmetics and may be solid, semisolid or liquid at room temperature. Preferably, a part of or all of the unctuous agent (B) is liquid at room temperature. Examples of the unctuous agent (B) include natural animal or plant oils, semisynthetic oils, hydrocarbon oils, higher fatty acids, higher alcohols, ester oils, glyceride oils, silicone oils and fluorine-containing oils.

Examples of the animal or plant oils and semisynthetic oils include avocado oil, linseed oil, almond oil, Ibota wax, perilla oil, olive oil, cacao butter, kapok wax, kaya oil, carnauba wax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methylester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil, wherein "POE" represents polyoxyethylene.

Examples of the hydrocarbon oils include ozokerite, α-olefin oligomers, light isoparaffin, light liquid isoparaffin, squalane, sysnthetic squalane, plant squalane, squalene, ceresin, paraffin, paraffin wax, liquid paraffin, liquid isoparaffin, pristane, polyisobutylene, microcrystalline wax, and Vaseline.

Examples of the higher fatty acids induce lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

Examples of the ester oils include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate.

Examples of the glyceride oils include acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

The unctuous agent (B) having a sterol backbone can form a stable emulsion by forming a complex with the silicone polymer (A). Examples of the unctuous agent (B) having a sterol backbone include sterols such as cholesterol, ergosterol, lanosterol, phytosterol, estradiol; alkylene oxide additive of sterols having hydroxyl group such as polyoxyethylene phytosterol, polyoxyethylene phytostanol, and polyoxyethylene cholestanol; and esters of higher fatty acids with sterols having hydroxyl group such as cholesteryl stearate, phytosteryl isostearate, and phytosteryl palmitate. Preferably, 100 parts by mass of the compound is used for 1 to 50 parts by mass of the silicone polymer (A). Particularly, use may be made of 100 parts by mass of the compound having a sterol backbone, 1 to 50 parts by mass of the silicone polymer (A), and 100 to 1000 parts by mass of a water soluble polyhydric alcohol selected from the group consisting of propylene glycol, dipropylene glycol, diethylene glycol, 3-methyl-3-butene-1-ol, 1,3-butylene glycol, glycerin, and diglycerin.

Examples of the silicone oils include those of the following formulas.

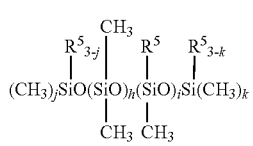

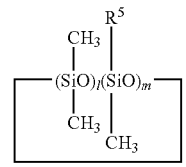

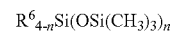

wherein $R^5$ is selected from the group consisting of a hydrogen atom, a hydroxyl group, alkyl or fluorinated alkyl groups having 2 to 20 carbon atoms, aryl groups, aminoalkyl groups, $C_{6-22}$ alkoxy groups and a group of the formula, $(CH_3)_3SiO[(CH_3)_2SiO]_p Si(CH_3)_2CH_2CH_2-$, wherein p is an integer of from 0 to 500. $R^6$ is a $C_{1-20}$ alkyl group. In the formula (8), h is an integer of from 0 to 1000, i is an integer of from 0 to 1000, provided that h+i ranges from 1 to 2000, each of j and k is 0, 1, 2 or 3. In the formula (9), l and m are integers of from 0 to 8, with l+m ranging from 3 to 8, and, in the formula (10), n is an integer of from 1 to 4.

Examples of $R^5$ include methyl, ethyl, propyl, butyl, hexyl, octyl, decyl, dodecyl, tetradecyl, hexadecyl, octadecyl, trifluoropropy, nonafluorohexyl, heptadecylfluorodecyl, phenyl, aminopropyl, dimetylaminopropyl, aminoethylaminopropyl, stearoxy, butoxy, ethoxy, propoxy, cetyloxy, myristyloxy, styryl, and α-methylstylyl, among which hexyl, octyl, decyl, dodecyl, dodecyl, tetradecyl, hexadecyl, octadecyl, trifluoropropy, phenyl, aminopropyl, and aminoethylaminopropyl are preferred.

Examples of the silicone oils include organopolysiloxanes having low or high viscosity, such as dimethylpolysiloxane, methylphenylpolysiloxane, methylhydrogenpolysiloxane and dimethylsiloxane-methylphenylsiloxane copolymer; cyclosiloxanes, such as octamethylcyclotetrasiloxane(D4), decamethylcyclopentasiloxane(D5), dodecamethylcyclohexasiloxane(D6), tetramethyltetrahydrogencyclotetrasiloxane(H4), and tetramethyltetraphenylcyclotetrasiloxane; tristrimethylsiloxysilane (M3T), tetrakistrimethylsiloxysilane(M4Q); branched siloxane such as tristrimethylsiloxypropylsilane, tristrimethylsiloxybutylsilane, tristrimethylsiloxyhexylsilane, and tristrimethylsiloxyphenylsilane; higher alcohol-modified silicone such as stearoxysilicone; alkyl-modified silicone, amino-modified silicone and fluoro-modified silicone.

Examples of the fluorinated oil include perfluoropolyethers, perfluorodecaline, perfluorooctane, fluorinated pitch, fluoroalcohol and a combination thereof.

A content of the unctuous agent (B) may be varied from 1.0 to 99 mass %, depending on the form of the cosmetic, and preferably from 1.0 to 50.0 mass %, based on a total mass of the cosmetic according to the form of the cosmetic. Preferably, the content ranges from 1.0 to 5.0 mass %, based on a total mass of the cosmetic. If the content is less than the aforesaid lower limit, effects of the unctuous agent (B) may not be significant. If it exceeds the aforesaid upper limit, the effect of the present polymer (A) may not be significant.

The cosmetics of the present invention may further comprise one or more of (C) compound having an alcoholic hydroxyl group except the higher alcohol already mentioned above. Preferably, a water soluble mono- or polyhydric alcohol having 2 to 10 carbon atoms is used. A content of the compound (c) in the cosmetic is adjusted depending on a form of the cosmetic. Preferably, the content ranges from 0.1 to 50.0 mass %, based on a total mass of the cosmetic. Below the aforesaid lower limit, enough effect of moisturizing, antibacterial or antifungal may not be attained. A cosmetic comprising the compound (C) more than the aforesaid upper limit may be too sticky.

Examples of the compound having alcoholic hydroxyl group (C) include lower monohydric alcohols such as ethanol, propanol, and isopropanol; polyhydric alcohols such as ethylene glylcol, propylene glycol, 1,3-butylene glycol, diethylene glylcol, dipropylene glycol, polyethylene glycol, 3-methyl-3-butene-1-ol, glycerin, diglycerin, and triglycerin; and sugar alcohols such as sorbitol and maltose.

The present cosmetic may contain (D) a water-soluble polymer, water-swellable polymer or a mixture thereof. Examples of these water-soluble or water-swellable polymer include gum Arabic, tragacanth gum, arabinogalactan, locust bean gum (carob gum), guar gum, karaya gum, carrageenan, pectin, agar-agar, quince seed (i.e., marmelo), starch from rice, corn, potato or wheat, algae colloid, and trant gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, polyvinylpyrrolidone, and carboxyvinyl polymer; polyoxyethylene polymers such as polyethylene glycol; polyoxyethylene/polyoxypropylene copolymers; acrylic polymers such as sodium polyacrylate, polyethyl acrylate, and polyacrylamide; polyethyleneimine; cationic polymers; and inorganic thickening agents such as, bentonite, aluminum magnesium silicate, montmorillonite, videlite, nontronite, saponite, hectorite, and silicic anhydride. Film forming polymers such as polyvinyl alcohol and polyvinylpyrollidone are also included.

An amount of the water-soluble or water-swellable polymer (D) in the cosmetic ranges preferably from 0.01 to 25 mass %, based on a total mass of the cosmetic. If contained below the aforesaid lower limit, enough effect of thickening and/or film forming may not be attained. If contained above the aforesaid upper limit, it may cause stickiness.

The present cosmetic may contain (E) water. An amount of water in the cosmetic is preferably adjusted depending on the form of the cosmetic in the range of from 1 to 90.0 mass %, based on a total mass of the cosmetic. A cosmetic containing water less than the aforesaid lower limit may not give moisturizing feel to the skin. A cosmetic containing water more than the aforesaid upper limit may decrease adhesion to the skin.

The present cosmetic may optionally contain (F) powder, (G) surfactant, (H) crosslinked organopolysiloxane, (I) silicone resin which is gummy or solid at room temperature, and (J) conventionally used acrylic silicone resin and (K) UV-ray protective agent.

As the powder (F), any powder which are commonly used in cosmetics may be used, regardless of the shape such as spherical, spindle forms, acicular, and plate-like; particle size such as fume size, fine particles and pigment grade; and particle structure such as porous and non-porous. Examples of the powder include inorganic powder, organic powder, metal salt powder of surface active agent, colored pigments, pearl pigments, metallic powder pigments, and natural colors and the like.

Examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolitre, zeolite, ceramics powder, calcium secondary phosphate, alumina, aluminum hydroxide, boron nitride, and silica.

Examples of organic powder include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, cellulose, silk powder, nylon powder such as Nylon 12 and Nylon 6, spherical powder of crosslinked dimethylsilicone elastomer (Japanese Patent Application Laid-open No. 3-93834), spherical powder of polymethylsylsesquioxane (Japanese Patent Application Laid-open No. 3-47848), spherical powder of silicone elastomer coated with polymethylsylsesquioxane (Japanese Patent Application Laid-open No. 7-196815), styrene/acrylic acid copolymer, divinylbenzene/styrene copolymer, vinyl resin, urea resin, phenol resin, fluororesin, silicone resin, acrylic resin, melamine resin, epoxy resin, polycarbonate resin, microcrystalline fiber powder, starch powder, and lauroyl lysine.

Examples of metal salt of surface active agent (metal soaps) include zinc stearate, aluminum stearate, calcium stearate, magnesium stearate, zinc myristate, magnesium myristate, zinc cetyl phosphate, calcium cetyl phosphate, and zinc/sodium cetyl phosphate.

Examples of colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, in organic blue pigments such as Prussian blue and ultramarine blue, lakes of tar pigments, lakes of natural dyes, and synthetic resin powder such as a composite of these powder.

Examples of pearl pigments include titanium oxide-coated mica, titanium oxide-coated mica, bismuth oxychloride, titanium oxide-coated bismuth oxychloride, titanium oxide-coated talc, fish scales, and titanium oxide-coated colored mica; metallic powder pigments such as aluminum powder, copper powder and stainless powder.

Examples of tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural pigments such as carminic acid, laccaic acid, carthamin, brazilin, and crocin.

The powder may be in the form of composite or may be treated with silicone oil, fluorine compound, or surfactant to the extent not to adversely affect the present cosmetic. For example, the powder may or may not be treated beforehand with fluorine compound, silicone resin, silane coupling agent, titanium coupling agent, unctuous agent, N-acyl lysine, polyacrylic acid, metal surfactant, amino acid, inorganic compound; treatment of pendants; plasma treatment, or mechanochemical treatment. Two or more of the treatment may be employed.

Preferably, silicone elastomer spherical powder, polyethylene powder, polypropylene powder, polytetrafluoroethylene powder, polymethylsilsesquioxane spherical powder, silicone elastomer spherical powder coated with polymethylsilsesquioxane, and polyurethane powder are used to attain good stability with time and feel to the touch.

A content of the powder (F) in the cosmetic may vary depending on the form of the cosmetic. Generally, the content ranges from 0.1 to 50 mass %, preferably from 0.5 to 30 mass %, based on a total mass of the cosmetic.

As the surfactant (G), any surfactants such as anionic, cationic, nonionic or amphoteric surfactants commonly used in cosmetics can be used.

Examples of the anionic surfactants include fatty acid soaps, such as sodium stearate and triethanolamine palmitate, alkylether carboxylic acids and salts thereof, salts of condensates of amino acids with fatty acids, alkyl sulfonate salts, alkenesulfonates, sulfonates of fatty acid esters, fatty acid amide sulfonates, sulfonate salts of the formalin condensates, salts of alkyl sulfates, salts of secondary higher alcohol sulfates, salts of alkyl/allyl ether sulfates, salts of fatty acid ester sulfates, salts of fatty acid alkylolamide sulfates, and salts of Turkey Red oil salfate, alkyl phosphate salts, ether phosphate salts, alkylallylether phosphate salts, amide phosphate salts, and N-acylamino surfactants.

Examples of the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylenehydrogenatedcastoroil, polyoxyethylenephytostanol ether, polyoxyethylene phytosterol ether, polyoxyethylene cholestanol ether, polyoxyethylene cholesteryl ether, polyoxyalkylene-modified organopolysiloxane (Japanese Patent No. 2137062, Japanese Patent Application Laid-Open No. 7-330907), polyglycerin-modified organopolysiloxane (Publication of Examined Japanese Patent Application No. 62-34039, Japanese Patent No. 2613124, Japanese Patent No. 2844453, Japanese Patent Application Laid-Open No. 2002-179798), polyoxyalkylene/alkyl-comodified organopolysiloxane (Japanese Patent Application Laid-Open No. 61-90732, Japanese Patent Application Laid-Open No. 9-59386), alkanolamide, sugar ethers, and sugar amides.

Examples of the amphoteric surfactants include betaine, aminocarboxylates, and imidazoline derivatives. A content of the surfactant (G) preferably ranges from 0.1 to 20 mass %, more preferably from 0.5 to 10 mass %, based on a total mass of the cosmetic.

The crosslinked organopolysiloxane (H) may be prepared by reacting alkyhydrogenpolysiloxane with a crosslinker having a vinylic unsaturation group at an end of a molecule. Examples of the alkyhydrogenpolysiloxane include linear or branched methylhydrogenpolysiloxane, methylhydrogenpolysiloxane grafted with an $C_{6-20}$ alkyl chain, methylhydrogenpolysiloxane grafted with a polyoxyethylene. Two or more of hydrogen atoms bonded to silicon atoms are necessary on average. Examples of the crosslinker having two or more or vinylic reactive sites per molecule include methylvinylpolysiloxane, α,ω-alkenyldiene, glycerin triallyl ether, polyoxyalkynylated glycerin trially ether, trimethylolpropane trially ether, polyoxyalkynylated trimethylolpropane trially ether. The crosslinked organopolysiloxane preferably has at least one moiety selected from the group consisting of polyoxyalkylene group, polyglycerin residue, alkyl group, alkenyl group, aryl group, and fluoroalkyl group. Preferred examples of the crosslinked organopolysiloxane are those described in Japanese Patent Application Laid-Open No. 2-43263, Japanese Patent Application Laid-Open No. 2-214775, Japanese Patent No. 2631772, Japanese Patent Application Laid-Open No. 9-136813, Japanese Patent Application Laid-Open No. 2001-342255, WO03/20828, and WO03/24413. By using the crosslinked organopolysiloxane, effects are attained such as non-shiny finish, mat finish, improved adherence, and no color migration.

Preferably, the crosslinked organopolysiloxane (H) is swelled with a silicone unctuous agent (B) having a low viscosity of from 0.65 mm$^2$/sec to 10.0 mm$^2$/sec (25° C.) in a larger amount than the organopolysiloxane itself, for example, silicone oils, hydrocarbon oils, or ester oils. Examples of the crosslinked organopolysiloxane swelled with silicone oil are KSG-6, 16, 15, 16, 17, 18, 21, 24, 210, 710, 1610; examples of those swelled with hydrocarbon oil include KSG-31, 32, 34, 310, 320, 340, 41, 42, 44, 810, 820, 840; and examples of those swelled with ester oil include KSG-33, 330, 43, 830, all from Shin-Etsu Chemical Co., Ltd.

A content of the crosslinked organopolysiloxane (H) ranges preferably from 0.1 to 30 mass %, more preferably from 1 to 10 mass %, based on a total mass of the cosmetic. When the crosslinked organopolysiloxane (H) is swelled with the unctuous agent, the content depends on the type and quantity of the unctuous agent and ranges preferably from 0.5 to 60 mass %, more preferably from 2 to 50 mass %, most preferably from 3 to 40 mass % as the swelled organopolysiloxane.

As the gummy or solid silicone resin which is soluble in decamethylcyclopentasiloxane (I), preferred gummy silicone resin is the linear silicone of the formula, $(CH_3)_3SiO\{(CH_3)_2SiO\}_r\{(CH_3)R^3SiO\}_s(CH_3)_3$, wherein $R^3$ is a methyl, $C_{6-20}$ alkyl, aminoalkyl, fluorinated alkyl, or a quarterly ammonium group substituted $C_{3-15}$ alkyl group, r ranges from 1001 to 20000, s ranges from 1 to 5000, provided that r+s ranges from 2500 to 25000. Examples of preferred solid silicone resin include silicone network compounds which are combinations of M, T, D, and Q units such as MQ, MDQ, MTQ, MDTQ, TD, TQ, TDQ resin, wherein M is a trialkylsiloxy unit, D is a dialkylsiloxy unit, T is a trialkylsiloxy unit, and Q is tetra functional siloxy unit. Particularly preferred are the silicone network compounds having at least one moiety selected from the group consisting of pyrrolidone residue, long-chain alkyl groups, polyoxyalkylene groups, and fluoroalkyl groups (See Japanese Patent Application Laid-Open No. 2000-234062, Japanese Patent No. 3218872).

A content of the silicone resin (I) ranges preferably from 0.1 to 20 mass %, more preferably from 1 to 20 mass %, based on a total mass of the cosmetic.

In the present invention, the acrylic silicone resin (J) is a conventionally used acrylic silicone resin and not the present silicone polymer (A). Preferably, the acrylic silicone resin (J) is semi-solid or solid at room temperature. More preferably, the acrylic resin has at least one moiety selected from the group consisting of pyrrolidone residue, long-chain alkyl groups, polyoxyalkylene moieties, fluoroalkyl groups. The acrylic silicone resin may be a silicone- or acrylic-graft copolymer or block copolymer of silicone and acrylic backbones. (See Japanese Patent Application Laid-Open No. 1-319518, Japanese Patent No. 2704730, Japanese Patent No. 2767633, Japanese Patent No. 2767636, Japanese Patent Application Laid-Open 2000-344829.)

The acrylic silicone resin (J) may be incorporated in the cosmetic as it is or in the form of solution in a volatile or non-volatile silicone or hydrocarbon oil. A content of the acrylic silicone resin (J) ranges preferably from 0.1 to 20 mass %, more preferably from 1 to 10 mass %, based on a total mass of the cosmetic.

Examples of the UV-ray protective agent (K) include those of the aforesaid inorganic pigments and metal powder which can scatter UV-ray and organic UV-ray absorber. The UV-ray scattering inorganic pigments or metal powder are preferably incorporated in the cosmetic in the form of dispersion in the unctuous agent. Examples of the dispersion of UV-ray scattering titanium oxide in decamethylcyclopentasiloxane (D5) are SPD-T1, T2, T1S, T1V, T3V, and T5, all from Shin-Etsu Chemical Co. Ltd. Examples of the dispersion of UV-ray scattering zinc oxide in decamethylcyclopentasiloxane (D5) are SPD-Z1, Z2, Z3, Z1S, Z3S, and Z5, all from Shin-Etsu Chemical Co. Ltd. In place of D4, other unctuous agents such as M3T, M4Q, volatile or non-volatile hydrocarbon oils can be used.

Examples of the ultraviolet light absorbents include those of benzoic acid derivative type, such as p-aminobenzoic acid, ethyl p-aminobenzoate, and glyceryl p-aminobenzoate, p-dimethylaminoamyl bezoate, p-dimethylaminooctyl bezoate, 4-[N,N-di(2-hydroxypropyl)amino]ethyl benzoate; those of salicylic acid derivative type such as methyl salicylate, ethylene glycol salicylate, phenyl salicylate, octyl salicylate, benzyl salicylate, p-tert-phenyl butylphenyl salicylate, and homomentyl salicylate; those of cinnamic acid such as benzyl cinnamate, 2-ethoxyethyl-p-methoxy cinnamate, glyceryl mono-2-ethylhexanoyl-di-p-methoxy cinnamate; urocanic acid and, ethyl urocanate; those of benzophenone type such as hydroxymethoxy benzophenone, hydroxymethoxy benzophenone sulfonic acid, sodium hydroxymethoxy benzophenone sulfonate, dihydroxymethoxy benzophenone, sodium dihydroxydimethoxy benzophenone sulfonate, 2,4-dihydroxy benzophenone, and tetrahydroxy benzophenone; dibenzoyl methane type such as 4-tert-butyl-4'-methoxy-dibenzoyl methane; those of anthranilic acid type, such as methyl anthranilate; benzotriazol type such as 2-(2-hydroxy-5-methylphenyl)benzotriazol; and higher molecular weight derivatives thereof, silane derivatives and siloxane derivative thereof.

A content of the UV-ray protective agent (K) ranges preferably from 0.1 to 20 mass %, more preferably from 1 to 20 mass %, based on a total of the cosmetic. Particularly preferred UV-ray protective agents are 2-ethylhexyl p-methoxy cinnamate, and 4-t-butyl-4'-methoxy-dibenzoylmethane.

A UV-ray protective agent (K) encapsulated in polymer powder can be used. The polymer powder may or may not be hollow. Preferably, a diameter of primary particle of the powder ranges from 0.1 to 50 µm with a broad or sharp diameter distribution. Examples of the powder include acrylic, methacrylic, polystyrene, polyurethane, polyethylene, polypropylene, polyethylene terephthalate, silicone, polyamide, and acrylamide resins. Preferably, 0.1 to 30 mass % of an organic UV-ray protective agent, particularly a UV-A absorber, 4-t-butyl-4'-methoxy dibenzoylmethane, is contained in the polymer powder.

In the cosmetic of the present invention, other components that are commonly used in cosmetics can be incorporated in an amount not to adversely affect the cosmetic. Examples of the components include film forming agent, oil-soluble gelling agents, clay minerals modified with organic compounds, resins, moisture retention agents, antiseptics, anti-microbial agents, perfumes, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, and clathrate compounds.

Examples of the oil-soluble gelling agent include metal soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrin palmitic acid ester, dextrin stearic acid ester and dextrin 2-ethylhexaminic acid palmitic acid ester; inulin fatty acid esters such as fructooligostearate; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of a moisture retention agent include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

Examples of the antiseptics include alkyl p-oxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide and phenoxyethanol.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediamine tetraacetate, sodium polyphosphate, sodium metaphosphate and phosphoric acid. examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents include placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H;

vitamin P; nicotinic acids, such as nicotinic acid, benzyl nicotinate and nicotinic acid amide; pantothenic acids, such as calciumpantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

Preferred cosmetics are skincare cosmetic, hair cosmetic, antiperspirant, makeup cosmetic, and UV-ray protective soemetic. Examples include basic cosmetics such as milky lotion, cream, lotion, calamine lotion, sun screen agent, suntan agent, after shave lotion, pre-shave lotion, pack, cleansing, face wash, and cosmetic for acne protection; makeup cosmetic such as face foundation, powder, foundation, eye shadow, eyeliner, eyebrow, rouge, lipstick and nail color; hairdressing products, such as shampoo, rinse, conditioner, hair color, hair tonic, setting agent, body powder, deodorant, hair remover, soap, body shampoo, bath powder, hand soap, and perfume.

Further, the present cosmetic materials may be in various forms such as liquid, emulsion, solid, paste, gel, powder, pressed, laminated, mousse, spray, stick, and pencil forms.

EXAMPLES

The present invention will be explained in detail with reference to the following Examples but not limited to them. In the followings, "%" means "% by mass" unless otherwise specified, and viscosity was measured at 25 degrees C.

Preparation Examples 1 to 4

To a glass flask equipped with a stirrer, a thermometer, and a reflux condenser were placed organopolysiloxane represented by the following formula (11), 2-methacryloyloxyethyl phoshorylcholine represented by the following formula (12), methyl methacrylate, 2-propanol, and dimetyl-2,2'-azobis(2-methylpropionate), each in parts by mass indicated in Table 1, and heated under nitrogen flow to perform polymerization at 80 degrees C. for 10 hours. Under reduced pressure, volatile components were distilled off to obtain a silicone polymer. The number average molecular weights, determined by GPC with polystyrene standards, of the polymers, were as shown in Table 1.

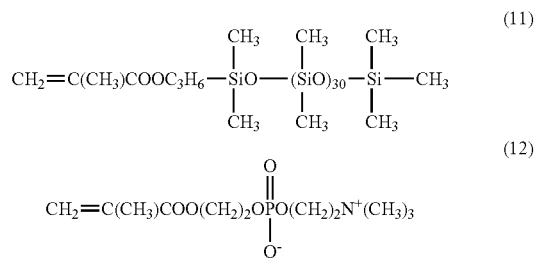

TABLE 1

Formulation and Molecular Weight of the Copolymers

|  | Prep. Ex.***) 1 | Prep. Ex. 2 | Prep. Ex. 3 | Prep. Ex. 4 |
|---|---|---|---|---|
| Organopolysiloxane | 50 | 50 | 10 | 90 |
| 2-Methacryloyloxyethyl phoshorylcholine | 5 | 5 | 80 | 5 |
| Methyl methacrylate | 45 | 45 | 10 | 5 |
| 2-Propanol | 120 | 120 | 120 | 120 |
| Catalyst*) | 1 | 5 | 1 | 5 |
| Appearance | Solid | Gummy | Solid | Liquid |
| (Viscosity in mm²/s) | (—) | (—) | (—) | (320) |
| Molecular weight of the polymer | 102000 | 33000 | 153000 | 9100 |
| Compatibility with decamethylcyclopentasiloxane**) | Translucent, homogeneously soluble | Translucent, homogeneously soluble | Insoluble | Transparent, homogeneously soluble |
| Compatibility with water**) | Insoluble | Insoluble | Transparent, homogeneously soluble | soluble |

*)Dimetyl-2,2'-azobis(2-methylpropionate)
**)10 parts by mass of a polymer and 90 parts by mass of decamethylcyclopentasiloxane or water were mixed, stirred at a room temperature for 10 hours, and then the status was observed visually.
***)Preparation Example As seen from Preparation Examples 1 and 2, molecular weight of a polymer can be changed even if the formulation in the copolymer is the same and, therefore, polymers which can provide films with different film strength can be obtained. As seen from Preparation Examples 2 and 4, it is possible to obtain desired polymers in various forms from solid to liquid by changing formulation in copolymerization. As seen from comparison of Preparation Examples 1, 2, and 4 with Preparation Example 3, it is possible to obtain polymers having different polarity, for instance, a lipo-soluble polymer or a water-soluble polymer, and it is possible to prepare silicone polymers having desired properties according to intended use of each cosmetic.

Preparation Examples 5 to 7, Comparative
Preparation Examples 1 to 2, Preparation Examples
1 to 5, and Comparative Examples 1 to 3

To a glass flask equipped with a stirrer, a thermometer, and a reflux condenser were placed organopolysiloxane represented by the above-described formula (11), 2-methacryloyloxyethyl phoshorylcholine represented by the above-described formula (12), 2-propanol, a reactive monomer, and dimetyl-2,2'-azobis(2-methylpropionate), each in parts by mass indicated in Table 2, and heated under nitrogen flow to perform polymerization at 80 degrees C. for 10 hours. Under reduced pressure, volatile components were distilled off to obtain silicone polymers. These polymers were colorless and transparent solid. The number average molecular weights reduced to polystyrene of the polymers, determined by GPC, were as shown in Table 2.

The averaged scores were calculated over all the test items, and the evaluation was made according to the following criteria.

Evaluation criteria:

Averaged score of 4.5 or higher A
Averaged score of 3.5 or higher and lower than 4.5 B

TABLE 2

Formulation and Molecular Weight of the Copolymers

|  | Prep. Ex. 5 | Prep. Ex. 6 | Prep. Ex. 7 | Com. Prep. Ex.**) 1 | Com. Prep. Ex. 2 |
|---|---|---|---|---|---|
| Organopolysiloxane | 30 | 36 | 15 | 0 | 30 |
| 2-methacryloyloxyethyl phoshorylcholine | 4 | 4 | 5 | 4 | 0 |
| Methyl methacrylate | 50 | 60 | 80 | 50 | 50 |
| Butyl methacrylate | 8 | 0 | 0 | 23 | 10 |
| 2-Ethylhexyl methacrylate | 8 | 0 | 0 | 23 | 10 |
| Catalyst*) | 2 | 2 | 2 | 2 | 2 |
| 2-Propanol | 120 | 120 | 120 | 120 | 120 |
| Mw of the polymer | 58,000 | 89,000 | 105,000 | 83,000 | 74,000 |

*)Dimetyl-2,2'-azobis(2-methylpropionate)
**)Comparative Preparation Example

Then, nail enamels were prepared using synthesized resins in the formulation indicated in Table 4 and the products were subjected to sensory test by a panel of ten people. The formulation amounts of each component are given in % by mass. The products were evaluated based on the following criteria for the following five items, i.e. sensory feel (whether a user feels tightened in the nails when a film dries), gloss (degree of gloss of a film after dried), adhesion (whether a film is fragile when the film after drying is scratched with nail), water resistance (whether a film exfoliates after bathing), and film durability (degree of preservation of a film after one week's daily life).

TABLE 3

| Score | Sensory Feel | Gloss | Adhesion | Water Resistance | Film Durability |
|---|---|---|---|---|---|
| 5 | Good (No tightened feel) | Good (Glossy) | Good (Not fragile) | Good (No exfoliation) | Good (No exfoliation) |
| 4 | Slightly good | Slightly good | Slightly good | Slightly good | Slightly good |
| 3 | Ordinary | Ordinary | Ordinary | Ordinary | Ordinary |
| 2 | Slightly bad | Slightly bad | Slightly bad | Slightly bad | Slightly bad |
| 1 | Bad (Tightened feel) | Bad (No gloss) | Bad (Fragile) | Bad (Exfoliated) | Bad (Exfoliated) |

Averaged score of 2.5 or higher and lower than 3.5 C
Averaged score of 1.5 or higher and lower than 2.5 D
Averaged score of lower than 1.5 E

TABLE 4

Formulation of Nail Enamels and Evaluation Results

| Component | Ingredients | Ex. 1 | Ex. 2 | Ex. 3 | Ex. 4 | Ex. 5 | Com. Ex. 1 | Com. Ex. 2 | Com. Ex. 3 |
|---|---|---|---|---|---|---|---|---|---|
| 1 | Nitro cellulose | 10 | 0 | 10 | 10 | 0 | 21 | 10 | 10 |
| 2 | Modified alkyd resin | 12 | 12 | 12 | 12 | 12 | 12 | 12 | 12 |
| 3 | Toluene sulfone amide resin | 5 | 5 | 5 | 5 | 5 | 5 | 5 | 5 |

TABLE 4-continued

Formulation of Nail Enamels and Evaluation Results

| Component | Ingredients | Ex. 1 | Ex. 2 | Ex. 3 | Ex. 4 | Ex. 5 | Com. Ex. 1 | Com. Ex. 2 | Com. Ex. 3 |
|---|---|---|---|---|---|---|---|---|---|
| 4 | Resin of Pre. Ex. 5 | 11 | 21 | 0 | 0 | 0 | 0 | 0 | 0 |
| 5 | Resin of Pre. Ex. 6 | 0 | 0 | 11 | 0 | 0 | 0 | 0 | 0 |
| 6 | Resin of Pre. Ex. 7 | 0 | 0 | 0 | 11 | 21 | 0 | 0 | 0 |
| 7 | Resin of Com. Prep. Ex. 1 | 0 | 0 | 0 | 0 | 0 | 0 | 11 | 0 |
| 8 | Resin of Com. Prep. Ex. 2 | 0 | 0 | 0 | 0 | 0 | 0 | 0 | 11 |
| 9 | Acetyltributyl citrate | 5 | 5 | 5 | 5 | 5 | 5 | 5 | 5 |
| 10 | Butyl acetate | 35 | 35 | 35 | 35 | 35 | 35 | 35 | 35 |
| 11 | Ethyl acetate | 17 | 17 | 17 | 17 | 17 | 17 | 17 | 17 |
| 12 | 2-Propanol | 5 | 5 | 5 | 5 | 5 | 5 | 5 | 5 |
| 13 | Organically modified bentonite | q.s. | q.s. | q.s. | q.s. | q.s. | q.s. | q.s. | q.s. |
| 14 | Pigments | q.s. | q.s. | q.s. | q.s. | q.s. | q.s. | q.s. | q.s. |
| Evaluation Results | Sensory feel | B | A | B | A | A | E | C | B |
| | Gloss | A | A | A | B | A | D | D | C |
| | Adhesion | A | B | B | A | A | B | B | E |
| | Water resistance | A | A | A | A | A | B | C | C |
| | Film durability | B | B | A | A | B | A | C | E |

Preparation Method

A. Component 2, a part of component 9 and Component 14 were mixed.

B. A part of component 1, a part of component 12 and Component 13 were mixed and kneaded sufficiently.

C. The residual part of Component 1, Component 3, Components 4 to 8, and the residual part of Component 9, Components 10 and 11, and the residual part of Component 12 were mixed and dissolved homogeneously.

D. Mixtures A and B were added to C and mixed until a homogeneous mixture is obtained.

As seen from Table 4, the nail enamels comprising the silicone polymer of the present invention were good in sensory feel, gloss, adhesion, water resistance, and film durability. Without nitro cellulose as a film ingredient, a good nail enamel could be obtained. Meanwhile, no satisfactory nail enamel was obtained when using a polymer in which either one of the oraganopolysiloxane and the phophorylcholine was copolymerized.

Preparation Examples 8 to 10, and Comparative Preparation Example 3

To the same glass flask as used in the above Preparation Examples, were placed organopolysiloxane represented by the following formula, 2-methacryloyloxyethyl phosphorylcholine represented by the above-described formula (12), 2-propanol, a reactive monomer, and dimetyl-2,2'-azobis(2-methylpropionate), each in parts by mass indicated in Table 5. Silicone polymers were obtained in the same manner as that in Preparation Example 1. The polymers were colorless and transparent solid. Their number average molecular weights reduced to polystyrene, determined by GPC, were as shown in Table 5. For Comparative Example, hydrophilic polyoxyethylene monomethacrylate or N-vinylpyrolidone were used instead of 2-methacryloyloxyethyl phosphorylcholine.

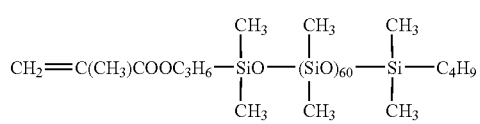

TABLE 5

Formulation and Molecular Weight of the Copolymers

| | Prep. Ex. 8 | Prep. Ex. 9 | Prep. Ex. 10 | Com. Prep. Ex. 3 |
|---|---|---|---|---|
| Organopolysiloxane | 60 | 55 | 60 | 60 |
| 2-methacryloyloxyethyl phoshorylcholine | 5 | 3 | 2 | 0 |
| Methyl methacrylate | 35 | 37 | 38 | 35 |
| polyoxyethylene monomethacrylate*) | 0 | 5 | 0 | 0 |
| N-vinylpyrolidone | 0 | 0 | 0 | 5 |
| 2-Propanol | 150 | 150 | 150 | 150 |
| Mw of polymer | 91000 | 120000 | 142000 | 98000 |

*)$CH_2$=$C(CH_3)COO(C_2H_4O)_{10}CH_3$

Then these resins were dissolved in 2-propanol to prepare solutions with a 30% concentration. These solutions were applied to glass plate of 15 cm long and 5 cm wide and 2-propanol was allowed to evaporate to form a film with a film thickness of 50 micron. The lower half of the glass plate was immersed in water for 1 hour. The dry part and the wet part of the film were rubbed with a finger and adhesion of the film was evaluated based on the following criteria. The results are shown in Table 6.

Evaluation Criteria:
A Good adhesion (no exfoliation of the film)
B Slightly exfoliated
C Approximately half exfoliated
D Half or more exfoliated
E Bad adhesion (most of all exfoliated)

TABLE 6

Evaluation results of the films

| | Resin film from Prep. Ex. 8 | Resin film from Prep. Ex. 9 | Resin film from Prep. Ex. 10 | Resin film from Com. Prep. Ex. 3 |
|---|---|---|---|---|
| Dry part of the film | A | A | A | C |
| Wet part of the film | A | B | B | D |

As a result, it is seen that a resin in which 2-methacryloyloxyethyl phoshorylcholine was copolymerized formed a film with a good adhesion when the film was dry. Although the 2-methacryloyloxyethyl phoshorylcholine is a hydrophilic monomer, the adhesion of the film was not impaired even when it was wet. Meanwhile, adhesion of the film of Comparative Preparation Example 3 was not satisfactory when it was dry and the adhesion of the film lowered significantly when it was wet with water.

Examples 6 to 9 and Comparative Examples 4 to 5

The oil-based foundations having the formulation indicated in the following Table 7 were manufactured and evaluated for sensory properties. The figures in the table are in % by mass.

TABLE 7

Formulation of the Oil-based Foundations

| Ingredient | Ex. 6 | Ex. 7 | Ex. 8 | Ex. 9 | Com. Ex. 4 | Com. Ex. 5 |
|---|---|---|---|---|---|---|
| 1. Ester of starch aliphatic acid | 6.0 | 6.0 | 6.0 | 6.0 | 6.0 | 6.0 |
| 2. Ceresin | 7.0 | 7.0 | 7.0 | 7.0 | 7.0 | 7.0 |
| 3. Polybutene | 4.0 | 4.0 | 4.0 | 4.0 | 4.0 | 4.0 |
| 4. Liquid paraffin | 28.0 | 28.0 | 28.0 | 28.0 | 28.0 | 28.0 |
| 5. Decamethylcyclopentasiloxane | 6.0 | 6.0 | 6.0 | 6.0 | 6.0 | 6.0 |
| 6. Copolymer of Prep. Ex. 5 | 6.0 | 0 | 0 | 0 | 0 | 0 |
| 7. Copolymer of Prep. Ex. 6 | 0 | 6.0 | 0 | 0 | 0 | 0 |
| 8. Copolymer of Prep. Ex. 8 | 0 | 0 | 6.0 | 0 | 0 | 0 |
| 9. Copolymer of Prep. Ex. 9 | 0 | 0 | 0 | 6.0 | 0 | 0 |
| 10. Copolymer of Com. Prep. Ex. 1 | 0 | 0 | 0 | 0 | 6.0 | 0 |
| 11. Copolymer of Com. Prep. Ex. 2 | 0 | 0 | 0 | 0 | 0 | 6.0 |
| 12. Titanium oxide | 33.0 | 33.0 | 33.0 | 33.0 | 33.0 | 33.0 |
| 13. Mica titanium | 3.0 | 3.0 | 3.0 | 3.0 | 3.0 | 3.0 |
| 14. Inorganic colored Pigments | 7.0 | 7.0 | 7.0 | 7.0 | 7.0 | 7.0 |
| 15. Antiseptic | q.s. | q.s. | q.s. | q.s. | q.s. | q.s. |
| 16. Fragrance | q.s. | q.s. | q.s. | q.s. | q.s. | q.s. |

Preparation Method
- A: Ingredients 1 to 12 were heat mixed.
- B: Ingredients 13 to 16 were mixed with A.
- C: B was dispersed homogeneously with a three roller mill.
- D: C was heat melted, then degassed, placed in a metal plate, and cooled to obtain a foundation.

Evaluation

A panel of 50 women tested the products. They rated each product for gloss on the product surface, extendability to skin, adhesive feel, affinity, non-stickiness, moisturized finish, beautiful finish, and durability of the makeup, based on the following criteria and the product was evaluated according to the averaged scores. The results are shown in Table 9.

TABLE 8

| Rating Criteria | | Evaluation Criteria |
|---|---|---|
| 5 | Very good | A Averaged score of 4.5 or higher |
| 4 | Good | B Averaged score of 3.5 or higher and lower than 4.5 |
| 3 | Ordinary | C Averaged score of 2.5 or higher and lower than 3.5 |
| 2 | Slightly bad | D Averaged score lower than 2.5 |
| 1 | Bad | |

TABLE 9

Evaluation results

| | Ex. 6 | Ex. 7 | Ex. 8 | Ex. 9 | Com. Prep. 4 | Com. Prep. 5 |
|---|---|---|---|---|---|---|
| Gloss on the product surface | B | B | A | A | D | C |
| Extendability to skin | A | A | A | A | D | C |
| Adhesive feel | A | A | A | A | B | D |
| Affinity | A | A | A | A | B | D |
| Non-stickiness | B | B | A | A | D | B |
| Moisturized finish | A | A | A | A | C | C |
| Beautiful finish | A | A | A | A | C | D |
| Durability of makeup | B | B | A | A | D | D |
| Total evaluation | B | B | A | A | C | D |

As seen from the results in Table 9, the oil-based foundations of Example 6 to 9 comprising the silicone polymer of the present invention were better in gloss on the product surface, extendability to skin, adhesive feel, affinity, non-stickiness, moisturized finish, beautiful finish, and durability of makeup, as compared to those comprising the polymer from Comparative Examples 4 and 5.

Preparation Examples 11 to 15, Reference Preparation Examples 1 to 2, Examples 10 to 14, and Reference Examples 1 to 2

To the same glass flask as used in the above Preparation Examples, were placed organopolysiloxane represented by the following general formula (13), wherein x, degree of polymerization, was varied, 2-methacryloyloxyethyl phoshorylcholine represented by the above formula (12), toluene, methyl methacrylate, and t-butylperoxyisopropyl monocabonate, each in parts by mass indicated in Tables 10 and 11 to obtain silicone polymers in the same manner as in Preparation Example 1. The polymerization was performed at a temperature of 100 degrees C. for 10 hours.

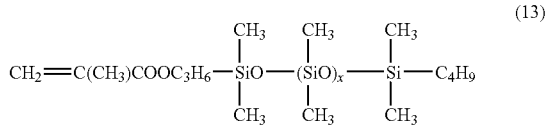

(13)

Preparation Method

Step A: Ingredients 1 to 20 were heat mixed.

Step B: Ingredients 21 to 25 were mixed homogeneously.

Step C: B was added to A and the mixture was made homogeneous.

The sensory test of the products was performed. The products were rated for gloss on the product surface, extendability to skin, adhesive feel, affinity, non stickiness, moisturized finish, beautiful finish, and durability of the makeup based on the following criteria and evaluated according to the averaged score.

TABLE 10

Formulation and Molecular Weight of the Copolymers

|  |  | Prep. Ex. 11 | Prep. Ex. 12 | Prep. Ex. 13 | Prep. Ex. 14 | Prep. Ex. 15 | Ref. Prep. Ex.***) 1 | Ref. Prep. Ex. 2 |
|---|---|---|---|---|---|---|---|---|
| Polymerization degree of organopolysiloxane, $x =$ | 20 | 55 | — | — | — | — | — | — |
|  | 40 | — | 55 | — | — | — | — | — |
|  | 60 | — | — | 55 | — | — | — | — |
|  | 150 | — | — | — | 55 | — | — | — |
|  | 250 | — | — | — | — | 55 | — | — |
|  | 350 | — | — | — | — | — | 55 | — |
|  | 0 | — | — | — | — | — | — | 55 |
| 2-methacryloyloxyethyl phoshorylcholine |  | 10 | 10 | 10 | 10 | 10 | 10 | 10 |
| Methyl methacrylate |  | 35 | 35 | 35 | 35 | 35 | 35 | 35 |
| Toluene |  | 120 | 120 | 120 | 120 | 120 | 120 | 120 |
| Catalyst*) |  | 2 | 2 | 2 | 2 | 2 | 2 | 2 |
| Molecular weight of the polymer |  | 93000 | 96000 | 84000 | 89000 | 105000 | 110000 | 76000 |
| Compatibility with decamethylcyclopentasiloxane**) |  | Slightly hazy | Translucent | Transparent | Transparent | Transparent | Translucent | Insoluble |

*)t-butylperoxyisopropyl monocarbonate
**)10 parts by mass of a polymer and 90 parts by mass of decamethylcyclopentasiloxane were mixed, stirred at a room temperature for 10 hours, and then the status was observed visually.
***)Reference Preparation Example Lipsticks having the formulation indicated in the following Table 11 were manufactured using these polymers and evaluated for their sensory properties.

TABLE 11

Formulation of the lipsticks

| Component | Ingredient | Ex. 10 | Ex. 11 | Ex. 12 | Ex. 13 | Ex. 14 | Ref.Ex. 1 | Ref. Ex. 2 |
|---|---|---|---|---|---|---|---|---|
| 1 | Candelilla Wax | 4.0 | 4.0 | 4.0 | 4.0 | 4.0 | 4.0 | 4.0 |
| 2 | Polyethylene Wax | 2.0 | 2.0 | 2.0 | 2.0 | 2.0 | 2.0 | 2.0 |
| 3 | KP561P*21) | 15.0 | 15.0 | 15.0 | 15.0 | 15.0 | 15.0 | 15.0 |
| 4 | Microcrystalline wax | 3.0 | 3.0 | 3.0 | 3.0 | 3.0 | 3.0 | 3.0 |
| 5 | Ceresin wax | 7.0 | 7.0 | 7.0 | 7.0 | 7.0 | 7.0 | 7.0 |
| 6 | Isotridecyl Isononanoate | 10.0 | 10.0 | 10.0 | 10.0 | 10.0 | 10.0 | 10.0 |
| 7 | Glyceryl Isostearate | 4.0 | 4.0 | 4.0 | 4.0 | 4.0 | 4.0 | 4.0 |
| 8 | KF6105*40) | 0.5 | 0.5 | 0.5 | 0.5 | 0.5 | 0.5 | 0.5 |
| 9 | Hydrogenated polyisobutene | 15.0 | 15.0 | 15.0 | 15.0 | 15.0 | 15.0 | 15.0 |
| 10 | Diisostearate maleate | 12.0 | 12.0 | 12.0 | 12.0 | 12.0 | 12.0 | 12.0 |
| 11 | Macadamia nut oil | 20.0 | 20.0 | 20.0 | 20.0 | 20.0 | 20.0 | 20.0 |
| 12 | Copolymer of Prep. Ex. 11 | 3.0 | — | — | — | — | — | — |
| 13 | Copolymer of Prep. Ex. 12 | — | 3.0 | — | — | — | — | — |
| 14 | Copolymer of Prep. Ex. 13 | — | — | 3.0 | — | — | — | — |
| 15 | Copolymer of Prep. Ex. 14 | — | — | — | 3.0 | — | — | — |
| 16 | Copolymer of Prep. Ex. 15 | — | — | — | — | 3.0 | — | — |
| 17 | Copolymer of Ref. Prep. Ex. 1 | — | — | — | — | — | 3.0 | — |
| 18 | Copolymer of Ref. Prep. Ex. 2 | — | — | — | — | — | — | 3.0 |
| 19 | Fragrance | q.s. | q.s. | q.s. | q.s. | q.s. | q.s. | q.s. |
| 20 | Antiseptics | q.s. | q.s. | q.s. | q.s. | q.s. | q.s. | q.s. |
| 21 | KP541*19) treated Red 202 | 0.8 | 0.8 | 0.8 | 0.8 | 0.8 | 0.8 | 0.8 |
| 22 | KP541*19) treated colcothar | 1.5 | 1.5 | 1.5 | 1.5 | 1.5 | 1.5 | 1.5 |
| 23 | KP541*19) treated iron oxide yellow | 1.0 | 1.0 | 1.0 | 1.0 | 1.0 | 1.0 | 1.0 |
| 24 | KP541*19) treated iron oxide black | 0.2 | 0.2 | 0.2 | 0.2 | 0.2 | 0.2 | 0.2 |
| 25 | KP541*19) treated titanium oxide | 1.0 | 1.0 | 1.0 | 1.0 | 1.0 | 1.0 | 1.0 |

TABLE 12

| Rating criteria | | Evaluation criteria |
|---|---|---|
| 5 | Very good | A Averaged score of 4.5 or higher |
| 4 | Good | B Averaged score of 3.5 or higher and lower than 4.5 |
| 3 | Ordinary | C Averaged score of 2.5 or higher and lower than 3.5 |
| 2 | Slightly bad | D Averaged score lower than 2.5 |
| 1 | Bad | |

The results are shown below.

TABLE 13

| | Evaluation results | | | | | | |
|---|---|---|---|---|---|---|---|
| | Ex. 10 | Ex. 11 | Ex. 12 | Ex. 13 | Ex. 14 | Ref Ex. 1 | Ref. Ex. 2 |
| Gloss on product surface | B | B | A | A | A | B | D |
| Extendability to skin | B | A | A | A | A | D | D |
| Adhesive feel | A | A | A | A | A | B | B |
| Affinity | A | A | A | A | A | C | C |
| Non-stickiness | B | A | A | A | A | C | D |
| Moisturized finish | B | B | A | A | A | D | C |
| Beautiful finish | B | B | A | A | A | B | D |
| Durability of makeup | B | B | A | A | A | B | D |
| Total evaluation | B | B | A | A | A | C | D |

As seen from Table 13, sensory properties are changed by the degree of organopolysiloxane. Therefore the degree of polymerization is preferably adjusted depending on the purposes of the cosmetics and prescriptions. Particularly, the degrees of polymerization in Examples 12 to 14 proved to be preferred for good sensory properties.

Preparation Example 16

A silicone polymer was obtained from 55 parts by mass of organopolysiloxane represented by the following formula (14), 35 parts by mass of methyl methacrylate, 2 parts by mass of glycerin monomethacrylate, 3 parts by mass of 2-methacryloyloxyethyl phoshorylcholine, 5 parts by mass of 2-ethylhexyl acrylate, 150 parts by mass of toluene, and 2 parts by mass of azobisisobutyronitrile in the same manner as that in Example 1. The polymer was colorless and transparent solid. The number average molecular weight reduced to polystyrene of the polymer, determined by GPC, was 223,000.

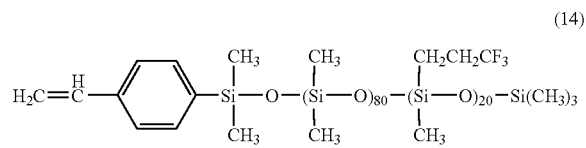

(14)

Preparation Example 17

A silicone polymer was obtained from 70 parts by mass of organopolysiloxane represented by the above-described formula (12), 20 parts by mass of 2-methacryloyloxyethyl phoshorylcholine, 10 parts by mass of glycerin monomethacrylate, 200 parts by mass of 2-propanol, and 2 parts by mass of t-butylperoxyisopropyl monocarbonate in the same manner as that in Example 1. This was colorless and transparent gummy solid. The number average molecular weight reduced to polystyrene of the polymer, determined by GPC, was 67,000.

Preparation Example 18

A silicone polymer was obtained from 80 parts by mass of organopolysiloxane represented by the above-described formula (12), 20 parts by mass of 2-methacryloyloxyethyl phoshorylcholine, 200 parts by mass of 2-propanol, and 2 parts by mass of t-butylperoxyisopropyl monocarbonate in the same manner as that in Example 1. This was colorless and transparent gummy solid and the number average molecular weight reduced to polystyrene, determined by GPC, was 46,000.

The polymers from Preparation Examples 1 to 16 were subject to the smell test, that is, a 100 ml glass bottle was charged with 10 parts by mass of each polymer, sealed, heated at a temperature of 80 degrees C. for 1 hour, and then unsealed to smell. It smelled slightly, probably, methyl methacrylate. However, for the polymers from Preparation Examples 17 and 18, no smell was detected in the same test. The reason for this seems that glycerin monomethacrylate and so on are non-volatile monomers. These non-volatile monomers can be formulated preferably in cosmetics without problem because they are not irritative to skin even when they remain in the polymers. When volatile monomers are used, remaining monomers can be removed by precipitating polymers into poor solvents, such as methanol, for purification.

Preparation Examples 19 to 22, Comparative Preparation Examples 4 to 5, Examples 15 to 18, and Comparative Examples 6 to 7

Silicone polymers were obtained according the formulation indicated in the following table in the same manner as in Preparation Examples 1. As a polymerization catalyst, 2.0 parts by mass of t-butylperoxyisopropyl monocarbonate was used and the polymerization conditions were 100 degrees C. and 10 hours.

TABLE 14

| | | Prep. Ex. 19 | Prep. Ex. 20 | Prep. Ex. 21 | Prep. Ex. 22 | Com. Prep. Ex. 4 | Com. Prep. Ex. 5 |
|---|---|---|---|---|---|---|---|
| Organopolysiloxane | Formula 15 below | 35 | — | — | — | — | — |
| | The same as used in Prep. Ex. 8 | — | 50 | 80 | 95 | — | — |
| 2-methacryloyloxyethyl phoshorylcholine | | 30 | 10 | 5 | 5 | 30 | 10 |
| Methyl methacrylate | | 25 | 35 | 15 | — | 50 | 30 |

TABLE 14-continued

|  | Prep. Ex. 19 | Prep. Ex. 20 | Prep. Ex. 21 | Prep. Ex. 22 | Com. Prep. Ex. 4 | Com. Prep. Ex. 5 |
|---|---|---|---|---|---|---|
| 2-Ethylhexyl acrylate | 10 | 5 | — | — | 20 | 60 |
| Toluene | 120 | 120 | 120 | 120 | 120 | 120 |
| Compatibility with decamethylcyclopentasiloxane*) | Slightly turbid | Translucent | Transparent | Transparent | Insoluble | Insoluble |
| Compatibility with water*) | Insoluble | Insoluble | Insoluble | Insoluble | Insoluble | Insoluble |

*)10 parts by mass of a polymer and 90 parts by mass of decamethylcyclopentasiloxane or water were mixed, stirred at a room temperature for 10 hours, and then the status was observed visually.

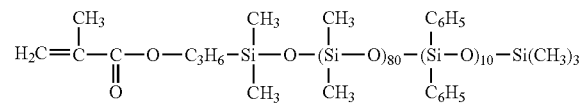

(15)

Each copolymer from Preparation Examples 18 to 21 was hydrophobic and insoluble in water but good in compatibility with decamethylcyclopentasiloxane.

Then these copolymers were formulated to prepare suncut creams of W/O type indicated below. The storage stability of the emulsion was observed visually after one month's storage at 50 degrees C. The judging criteria for storage stability were as follows.

A: not separated; B: slightly separated; C: separated; E: almost completely separated.

TABLE 15

Formulation of Suncut Creams

| Component | Ingredient | Ex. 15 | Ex. 16 | Ex. 17 | Ex. 18 | Com. Prep. 6 | Com. Prep. 7 |
|---|---|---|---|---|---|---|---|
| 1 | Decamethylcyclopentasiloxane | 17.5 | 17.5 | 17.5 | 17.5 | 17.5 | 17.5 |
| 2 | KP545*[20] | 6.0 | 6.0 | 6.0 | 6.0 | 6.0 | 6.0 |
| 3 | Glyceryl triisooctanoate | 5.0 | 5.0 | 5.0 | 5.0 | 5.0 | 5.0 |
| 4 | SPD-T5*[41] | 6.0 | 6.0 | 6.0 | 6.0 | 6.0 | 6.0 |
| 5 | KSG210*[5] | 5.0 | 5.0 | 5.0 | 5.0 | 5.0 | 5.0 |
| 6 | KF6017*[33] | 1.0 | 1.0 | 1.0 | 1.0 | 1.0 | 1.0 |
| 7 | SPD-Z1S*[44] | 20.0 | 20.0 | 20.0 | 20.0 | 20.0 | 20.0 |
| 8 | Copolymer of Prep. Ex. 19 | 6.0 | — | — | — | — | — |
| 9 | Copolymer of Prep. Ex. 20 | — | 6.0 | — | — | — | — |
| 10 | Copolymer of Prep. Ex. 21 | — | — | 6.0 | — | — | — |
| 11 | Copolymer of Prep. Ex. 22 | — | — | — | 6.0 | — | — |
| 12 | Copolymer of Com. Prep. Ex. 4 | — | — | — | — | 6.0 | — |
| 13 | Copolymer of Com. Prep. Ex. 5 | — | — | — | — | — | 6.0 |
| 14 | 1,3-butylene glycol | 2.0 | 2.0 | 2.0 | 2.0 | 2.0 | 2.0 |
| 15 | Sodium chloride | 0.5 | 0.5 | 0.5 | 0.5 | 0.5 | 0.5 |
| 16 | Antiseptics | q.s. | q.s. | q.s. | q.s. | q.s. | q.s. |
| 17 | Fragrance | q.s. | q.s. | q.s. | q.s. | q.s. | q.s. |
| 18 | Purified Water | Balance | Balance | Balance | Balance | Balance | Balance |
|  | Storage stability of emulsion | B | A | A | A | D | D |

Preparation Method

A: Ingredients 1 to 13 were mixed homogeneously.

B: Ingredients 14 to 18 were mixed homogeneously, added to A and stirred for emulsifying.

The sensory tests of the products were performed. The products were rated for extendability to skin, adhesive feel, non-stickiness, beautiful finish, and durability of makeup based on the criteria in the following table and evaluated according to averaged scores. The results are shown in Table 17.

TABLE 16

| Rating Criteria |  | Evaluation Criteria |  |
|---|---|---|---|
| 5 | Very good | A | Averaged score of 4.5 or higher |
| 4 | Good | B | Averaged score of 3.5 or higher and lower than 4.5 |
| 3 | Ordinary | C | Averaged score of 2.5 or higher and lower than 3.5 |
| 2 | Slightly bad | D | Averaged score lower than 2.5 |
| 1 | Bad |  |  |

TABLE 17

Evaluation Results

|  | Ex. 15 | Ex. 16 | Ex. 17 | Ex. 18 | Com. Prep. 6 | Com. Prep. 7 |
|---|---|---|---|---|---|---|
| Extendability to skin | B | A | A | A | D | D |
| Adhesive feel | A | A | B | B | B | C |

TABLE 17-continued

| | Evaluation Results | | | | |
|---|---|---|---|---|---|
| | Ex. 15 | Ex. 16 | Ex. 17 | Ex. 18 | Com. Prep. 6 | Com. Prep. 7 |
| Non-stickiness | A | A | A | A | C | D |
| Beautiful finish | B | B | B | A | D | D |
| Durability of makeup | A | A | A | A | D | D |
| Total evaluation | B | A | A | A | C | D |

For the cosmetics, such as suncut cream, in which water resistance is important, cosmetics with good sensory properties can be obtained by copolymerizing a given amount of organopolysiloxane with a phospholipid derivative so that the polymer will have a compatibility with decamethylcyclopentasiloxane.

Preparation Examples 22 to 25, Comparative Preparation Examples 6 to 7, Examples 19 to 22, and Comparative Examples 8 to 9

According the same manner as in Preparation Example 1, allyl silicone polymers were obtained from the ingredients with the formulation indicated in the following Table. As a polymerization catalyst, 2.0 parts by mass of t-butylperoxyisopropyl monocarbonate was used and the polymerization conditions were 100 degrees C. and 10 hours. All of the copolymers obtained were water-soluble.

TABLE 18

| | | Prep. Ex. 23 | Prep. Ex. 24 | Prep. Ex. 25 | Prep. Ex. 26 | Com. Prep. Ex. 7 | Com. Prep. Ex. 8 |
|---|---|---|---|---|---|---|---|
| Radically Polymerisable organopolysiloxane | Formula 10 above | 10 | 20 | — | — | — | 20 |
| | The same as used in Prep. Ex. 8 | — | — | 25 | 20 | — | — |
| 2-methacryloyloxyethyl phoshorylcholine | | 75 | 80 | 25 | 50 | 80 | — |
| Methyl methacrylate | | 10 | — | — | 10 | 10 | 20 |
| polyoxyethylene monomethacrylate*) | | 5 | — | 50 | 10 | 10 | — |
| Diglycerin monomethacrylate | | — | — | — | 10 | — | 60 |
| 2-Propanol | | 120 | 120 | 120 | 120 | 120 | 120 |

*)$CH_2$=$C(CH_3)COO(C_2H_4O)_{10}CH_3$

Then these copolymers were formulated to prepare hand creams of O/W type indicated in the following table.

TABLE 19

| | Formulation of Hand Creams | | | | | | |
|---|---|---|---|---|---|---|---|
| Component | Ingredient | Ex. 19 | Ex. 20 | Ex. 21 | Ex. 22 | Com. Prep. 9 | Com. Prep. 10 |
| 1 | KF7312J*[29] | 5.0 | 5.0 | 5.0 | 5.0 | 5.0 | 5.0 |
| 2 | KP561P*[21] | 8.0 | 8.0 | 8.0 | 8.0 | 8.0 | 8.0 |
| 3 | Cetyl alcohol | 1.0 | 1.0 | 1.0 | 1.0 | 1.0 | 1.0 |
| 4 | Glyceryl Triisostearate | 5.0 | 5.0 | 5.0 | 5.0 | 5.0 | 5.0 |
| 5 | Stearic Acid | 3.0 | 3.0 | 3.0 | 3.0 | 3.0 | 3.0 |
| 6 | Glyceryl Monostearate | 1.5 | 1.5 | 1.5 | 1.5 | 1.5 | 1.5 |
| 7 | KF6015*[32] | 0.7 | 0.7 | 0.7 | 0.7 | 0.7 | 0.7 |
| 8 | Sorbitan Sesquioleate | 0.5 | 0.5 | 0.5 | 0.5 | 0.5 | 0.5 |
| 9 | Polyoxyethylenesorbitan Monooleate | 1.0 | 1.0 | 1.0 | 1.0 | 1.0 | 1.0 |
| 10 | Copolymer of Prep. Ex. 23 | 5.0 | — | — | — | — | — |
| 11 | Copolymer of rep. Ex. 24 | — | 5.0 | — | — | — | — |
| 12 | Copolymer of Prep. Ex. 25 | — | — | 5.0 | — | — | — |
| 13 | Copolymer of Prep. Ex. 26 | — | — | — | 5.0 | — | — |
| 14 | Copolymer of Com. Prep. Ex. 6 | — | — | — | — | 5.0 | — |
| 15 | Copolymer of Com. Prep. Ex. 7 | — | — | — | — | — | 5.0 |
| 16 | MetholoseSM400*[47] (2% aq.sol.) | 7.0 | 7.0 | 7.0 | 7.0 | 7.0 | 7.0 |
| 17 | 1,3-butyleneglycol | 5.0 | 5.0 | 5.0 | 5.0 | 5.0 | 5.0 |
| 18 | Antiseptics | q.s. | q.s. | q.s. | q.s. | q.s. | q.s. |
| 19 | Fragrance | q.s. | q.s. | q.s. | q.s. | q.s. | q.s. |
| 20 | Purified Water | Balance | Balance | Balance | Balance | Balance | Balance |

Preparation Method

A: Ingredients 1 to 9 were mixed.

B: Ingredients 10 to 20 were mix dissolved.

C: A was added to B and stirred for emulsifying.

The sensory tests of the products were performed. The products were rated for extendability to skin, adhesive feel, affinity, non stickiness, moisturized finish, beautiful finish, and durability of makeup based on the criteria in the following table and evaluated according to the averaged scores.

TABLE 20

| Rating Criteria | | Evaluation Criteria |
|---|---|---|
| 5 | Very good | A Averaged score of 4.5 or higher |
| 4 | Good | B Averaged score of 3.5 or higher and lower than 4.5 |
| 3 | Ordinary | C Averaged score of 2.5 or higher and lower than 3.5 |
| 2 | Slightly bad | D Averaged score lower than 2.5 |
| 1 | Bad | E |

The results are shown in the following Table.

TABLE 21

| | Ex. 19 | Ex. 20 | Ex. 21 | Ex. 22 | Com. Prep. 9 | Com. Prep. 10 |
|---|---|---|---|---|---|---|
| Extendability to skin | A | A | A | A | D | B |
| Adhesive feel | A | A | B | B | B | D |
| Affinity | A | A | A | A | C | C |
| Non-stickiness | A | A | A | A | D | D |
| Moisturized finish | B | B | A | A | D | D |
| Beautiful finish | A | A | A | A | D | D |
| Durability of makeup | A | A | B | B | D | D |
| Total evaluation | B | B | A | A | C | D |

As seen from Table 21, a cosmetic with good sensory properties can be obtained from a polymer obtained by copolymerizing a given amount of organopolysiloxane with a phopolipid derivative.

Examples 23 to 25 and Comparative Examples 11 to 13

The lipsticks with the formulation indicated in the following Table were prepared and their sensory properties were evaluated.

TABLE 22

Formulation of Lipsticks

| Ingredient | Ex. 23 | Ex. 24 | Ex. 25 | Com. Prep. 11 | Com. Prep. 12 | Com. Prep. 13 |
|---|---|---|---|---|---|---|
| 1. Microcrystalline Wax | 6.0 | 6.0 | 6.0 | 6.0 | 6.0 | 6.0 |
| 2. Synthetic Hydrocarbon Wax | 8.0 | 8.0 | 8.0 | 8.0 | 8.0 | 8.0 |
| 3. Ceresin Wax | 5.0 | 5.0 | 5.0 | 5.0 | 5.0 | 5.0 |
| 4. Candelilla Wax | 2.0 | 2.0 | 2.0 | 2.0 | 2.0 | 2.0 |
| 5. Pentaerythrityl Rosinate | 5.0 | 5.0 | 5.0 | 5.0 | 5.0 | 5.0 |
| 6. Cetyl 2-Ethylhexanoate | 15.0 | 15.0 | 15.0 | 15.0 | 15.0 | 15.0 |
| 7. Glyceryl Trioctanoate | 20.0 | 20.0 | 20.0 | 20.0 | 20.0 | 20.0 |
| 8. Copolymer of Prep. Ex. 10 | 10.0 | 0 | 0 | 0 | 0 | 0 |
| 9. Copolymer of Prep. Ex. 15 | 0 | 10.0 | 0 | 0 | 0 | 0 |
| 10. Copolymer of Prep. Ex. 16 | 0 | 0 | 10.0 | 0 | 0 | 0 |
| 11. Copolymer of Com. Prep. Ex. 4 | 0 | 0 | 0 | 10.0 | 0 | 0 |
| 12. Copolymer of Com. Prep. Ex. 5 | 0 | 0 | 0 | 0 | 10.0 | 0 |
| 13. Copolymer of Com. Prep. Ex. 6 | 0 | 0 | 0 | 0 | 0 | 10.0 |
| 14. Methylphenylpolysiloxane | 10.0 | 10.0 | 10.0 | 10.0 | 10.0 | 10.0 |
| 15. Pigments | 5.0 | 5.0 | 5.0 | 5.0 | 5.0 | 5.0 |
| 16. Mica Titanium | 15.0 | 15.0 | 15.0 | 15.0 | 15.0 | 15.0 |
| 17. Fragrance | q.s. | q.s. | q.s. | q.s. | q.s. | q.s. |

Preparation Method

A: Components 1 to 15 were heat dissolved.

B: The mixture was degassed, formulated with Component 16, and then put into a container, and formed.

Evaluation

The products were rated for gloss on product surface, stickiness in application, adhesive feel in application, stickiness after application, adhesive feel after application, non color-transfer, non color-fading, and non color-bleeding based on the same criteria as in the above Table 20 and evaluated according to the averaged score. These results are shown in the following Table.

TABLE 23

| Evaluation Item | Ex. 23 | Ex. 24 | Ex. 25 | Com. Ex. 11 | Com. Ex. 12 | Com. Ex. 13 |
|---|---|---|---|---|---|---|
| Gloss on product surface | A | A | A | B | D | D |
| Stickiness in application | A | B | A | D | D | D |
| Adhesive feel in application | A | A | A | D | C | C |
| Stickiness after application | A | B | A | C | D | D |
| Adhesive feel after application | A | A | A | D | C | C |
| Non color-transfer | A | A | B | C | C | D |
| Non color-fading | A | A | A | C | D | C |
| Non color-bleeding | A | A | B | D | C | C |
| Total evaluation | A | A | A | D | D | D |

As seen from these results, the lipsticks of Examples 23 to 25 comprising the copolymers of the present invention were much more glossy on the product surface and less sticky in and after application compared to those of Comparative Examples 11 to 13. The lipsticks obtained were better in adhesive feel and durability without causing color-transfer, color-fading, or color-bleeding.

Examples 26 to 30

Creams of W/O type were prepared in the following formulation.

TABLE 24

| Component | Ingredient | Ex. 26 | Ex. 27 | Ex. 28 | Ex. 29 | Ex. 30 |
|---|---|---|---|---|---|---|
| 1 | KSG310*[10] | 6.0 | — | — | — | — |
| 2 | Isododecane | 13.5 | — | — | — | — |
| 3 | Macadamia nuts oil | 4.0 | 5.0 | — | 3.0 | — |
| 4 | KSG810*[15] | — | 7.0 | — | — | — |
| 5 | Liquid paraffin | — | 13.5 | — | — | — |
| 6 | KSG710*[14] | — | — | 7.0 | — | 5.0 |
| 7 | Dimethylpolysiloxane (viscosity 20 mm$^2$/s) | — | — | 10.0 | — | 11.5 |
| 8 | KSG840*[18] | — | — | — | 3.0 | — |
| 9 | KSG44*[9] | — | — | — | 2.0 | — |
| 10 | KSP100*[24] | — | 3.0 | — | 2.0 | — |
| 11 | KF6105*[40] | — | — | — | 0.5 | — |
| 12 | Squalan | — | — | — | 14.0 | — |
| 13 | Copolymer of Prep. Ex. 8 | 1.5 | — | — | 0.5 | — |
| 14 | Copolymer of Prep. Ex. 9 | — | 0.5 | — | — | 0.5 |
| 15 | Copolymer of Prep. Ex. 15 | — | — | 0.5 | — | — |
| 16 | Sodium citrate | 0.2 | 0.2 | 0.2 | 0.2 | 0.2 |
| 17 | Propylene glycol | 8.0 | 8.0 | — | — | — |
| 18 | Glycerin | 3.0 | 3.0 | — | 4.0 | — |
| 19 | Dipropylene glycol | — | — | 10.0 | 8.0 | 10.0 |
| 20 | Ethanol | — | — | 5.0 | — | 5.0 |
| 21 | Sodium chloride | — | — | — | 0.5 | 0.5 |
| 22 | Antiseptics | q.s. | q.s. | q.s. | q.s. | — |
| 23 | Fragrance | q.s. | q.s. | q.s. | q.s. | q.s. |
| 24 | Purified water | Balance | Balance | Balance | Balance | Balance |

Preparation Method

A: Components 1 to 17 were mixed.

B: Components 18 to 26 were mix dissolved and added to A for emulsifying.

The W/O type creams thus obtained could be extended lightly, had non-greasy and non-sticky touch, a good adhesive feel, and a good affinity, and provided mat and moisturized finish.

Examples 31 to 33

Suncare cosmetics were prepared in the following formulation.

TABLE 25

| Component | Ingredient | Suntan milky lotion Ex. 31 | Suntan cream Ex. 32 | Suncut milky lotion Ex. 33 |
|---|---|---|---|---|
| 1 | Emulsifying composition | 6.0 | — | — |
| 2 | Dimethylpolysiloxane (viscosity 6 mm$^2$/s) | 39.0 | 5.0 | 5.0 |
| 3 | Madamia nut oil | 4.0 | — | — |
| 4 | Decamethylcyclopentasiloxane | — | 15.0 | — |
| 5 | Isododecane | — | — | 3.0 |

TABLE 25-continued

| Component | Ingredient | Suntan milky lotion Ex. 31 | Suntan cream Ex. 32 | Suncut milky lotion Ex. 33 |
|---|---|---|---|---|
| 6 | Glyceryl triisooctanoate | — | — | 5.0 |
| 7 | KSG210[*5)] | — | — | 3.0 |
| 8 | KP561P[*21)] | — | 0.5 | — |
| 9 | KF6028[*37)] | — | 2.2 | — |
| 10 | KF6105[*40)] | — | — | 1.0 |
| 11 | SPD-T1S[*43)] | — | — | 20.0 |
| 12 | SPD-Z1S[*44)] | — | — | 30.0 |
| 13 | Palmitic acid | — | 0.2 | — |
| 14 | Dimethyloctyl para-aminobenzoate | — | 0.5 | — |
| 15 | 4-t-butyl-4'-methoxydibenzoylmethane | — | 0.5 | — |
| 16 | Kaolin | — | 0.5 | — |
| 17 | Colcothar | — | 0.2 | — |
| 18 | Iron oxide yellow | — | 0.3 | — |
| 19 | Iron oxide black | — | 0.1 | — |
| 20 | Titanium oxide treated mica | — | 1.0 | — |
| 21 | Copolymer of Prep. Ex. 17 | 10.0 | 10.0 | 10.0 |
| 22 | Sodium dehydroacetate | 0.2 | — | — |
| 23 | 1,3-butylene glycol | 5.0 | 5.0 | 3.0 |
| 24 | Sodium citrate | — | — | 0.5 |
| 25 | Sodium L-glutamate | — | 3.0 | — |
| 26 | Dioctadecyldimethylammonium chloride | — | 0.1 | — |
| 27 | Antioxidant | q.s. | q.s. | q.s. |
| 28 | Antiseptics | q.s. | q.s. | q.s. |
| 29 | Fragrance | q.s. | q.s. | q.s. |
| 30 | Purified water | Balance | Balance | Balance |

Mixing Ratio in the Emulsifying Composition a. KF6017[*33)] (polyether modified silicone from Shi-Etsu Chemical Co., Ltd.), 10.0 parts by mass b. Dioctadecylmethylammonium salt modified montmorillonite, 10.0 parts by mass c. Ethanol, 40.0 parts by mass Preparation Method of the Emulsifying Composition (1) Component "a" was dissolved in Component "C" and Component "b" was added.

(2) Mixture (1) was stirred with a disper for 1 hour, and then ethanol was removed with an evaporator.

(3) Mixture (2) was dried at 50 degrees C. for 24 hours to obtain the emulsifying composition.

Preparation Method

A: Components 1 to 21 were mixed homogeneously.

B: Components 22 to 30 were mixed homogeneously, then added to A, and stirred for emulsifying.

The suncare cosmetics thus obtained had fine texture and could be extended lightly. The cosmetics were non-sticky and non-greasy, and provided moisturized and refreshed sensory properties, while they were good in water resistance and makeup durability. The cosmetics did not change with temperature or with time and stability was good.

Examples 34 to 38

Cosmetics of W/O type were prepared in the following formulation.

TABLE 26

| Component | Ingredient | Antiperspirant Ex. 34 | UV cut cream Ex. 35 | UV cut milky lotion Ex. 36 | Makeup base Ex. 37 | Milky lotion Ex. 38 |
|---|---|---|---|---|---|---|
| 1 | KSG210[*5)] | 8.0 | 7.0 | — | 5.0 | — |
| 2 | Dimethylpolysiloxane (viscosity 6 mm²/s) | — | — | 5.0 | 6.0 | 6.0 |
| 3 | Dimethylpolysiloxane (viscosity 20 mm²/s) | — | — | — | 2.0 | — |
| 4 | KSG15[*1)] | — | — | — | 1.0 | — |
| 5 | Decamethylcyclopentasiloxane | 7.0 | 20.0 | — | 3.0 | 22.0 |
| 6 | KF6019[*35)] | — | — | — | — | 1.5 |
| 7 | KP545[*20)] | — | 12.0 | — | — | — |
| 8 | Glyceryl triisooctanoate | 8.0 | 3.0 | 2.0 | — | — |
| 9 | KSG710[*14)] | — | — | 6.0 | — | — |
| 10 | KF6104[*39)] | — | — | 0.5 | — | — |
| 11 | KF6017[*33)] | — | 1.5 | — | — | — |
| 12 | Silicone treated zinc oxide | — | 20.0 | — | — | — |
| 13 | Rheopearl TT[*48)] | — | — | — | — | 0.2 |
| 14 | Rheopearl ISK[*49)] | — | — | — | — | 1.8 |
| 15 | SPD-T5[*41)] | — | — | 30.0 | 10.0 | — |
| 16 | SPD-Z5[*42)] | — | — | 30.0 | — | — |
| 17 | Octyl methoxycinnamate | — | 6.0 | — | — | — |

TABLE 26-continued

| Component | Ingredient | Anti-perspirant Ex. 34 | UV cut cream Ex. 35 | UV cut milky lotion Ex. 36 | Makeup base Ex. 37 | Milky lotion Ex. 38 |
|---|---|---|---|---|---|---|
| 18 | Copolymer of Prep. Ex. 10 | 1.0 | 1.0 | 1.0 | 1.0 | 1.0 |
| 19 | 1,3-Butylene glycol | 5.0 | — | — | — | 7.0 |
| 20 | Dipropylene glycol | — | 3.0 | 3.0 | 5.0 | — |
| 21 | Sodium citrate | 0.2 | 0.2 | 0.2 | 0.2 | 0.2 |
| 22 | Aluminum chlorohydrate | 20.0 | — | — | — | — |
| 23 | Metholose 65-SH4000*46) (2% aq. sol.) | — | — | — | 2.5 | — |
| 24 | Ethanol | — | — | — | 3.0 | 5.0 |
| 25 | Antiseptics | q.s. | q.s. | q.s. | q.s. | q.s. |
| 26 | Fragrance | q.s. | q.s. | q.s. | q.s. | q.s. |
| 27 | Purified water | Balance | Balance | Balance | Balance | Balance |

Preparation Method

A: Components 1 to 18 were heat mixed.
B: Components 19 to 27 were dissolved homogeneously.
C: B was added to B and stirred for emulsifying.

The W/O type cosmetics thus obtained extended lightly, had non-sticky or non-greasy touch, and provided refreshed feel. The cosmetics did not change with temperature or with time and sensory properties and stability were also very good.

Examples 39 to 41

Creams of O/W type were prepared according to the following formulation.

TABLE 27

| Component | Ingredient | Ex. 39 | Ex. 40 | Ex. 41 |
|---|---|---|---|---|
| 1 | KSG16*2) | 8.0 | 15.0 | 28.0 |
| 2 | KSG18*3) | 2.0 | — | — |
| 3 | Isotridecyl isononanoate | 5.0 | — | — |
| 4 | Decamethylcyclopentasiloxane | — | 10.0 | 10.0 |
| 5 | KSG43*8) | — | 2.0 | — |
| 6 | Dimethylpolysiloxane (viscosity 6 mm²/s) | — | 18.0 | 5.0 |
| 7 | KF6100*38) | — | — | 0.7 |
| 8 | Copolymer of Prep. Ex. 13 | 2.0 | 2.0 | — |
| 9 | Copolymer of Prep. Ex. 18 | — | — | 2.0 |
| 10 | 1,3-Butylene glycol | — | — | 3.0 |
| 11 | Dipropylene glycol | 7.0 | 3.0 | — |
| 12 | Glycerin | 5.0 | — | — |
| 13 | Metholose SM400*47) (2% aq. sol.) | 7.0 | — | — |
| 14 | Spigel 305*50) | 2.0 | 0.8 | 0.8 |
| 15 | Guanine | 1.0 | — | — |
| 16 | Xanthan gum (2% Aqueous solution) | — | 8.0 | — |
| 17 | Polyoxyethylene hardened castor oil | — | — | 0.5 |
| 18 | Aristoflex AVC*51) (5% aq. sol) | — | — | 10.0 |
| 19 | Sodium chloride | — | — | 0.1 |
| 20 | Antiseptics | q.s. | q.s. | q.s. |
| 21 | Fragrance | q.s. | q.s. | q.s. |
| 22 | Purified water | Balance | Balance | Balance |

Preparation Method

A: Components 1 to 9 were mixed.
B: Components 10 to 22 were mix dissolved.
C: A was added to B and stirred for emulsifying.

The O/W type cosmetics thus obtained had fine texture and could be extended lightly. The cosmetics had non-sticky and non-greasy touch and provided moisturized and refreshed feel, while the makeup durability was good. They did not change with temperature or with time and had a good stability.

Examples 42 to 44

Hair creams were prepared in the following formulation.

TABLE 28

| Component | Ingredient | Ex. 42 | Ex. 43 | Ex. 44 |
|---|---|---|---|---|
| 1 | Tristrimethylsiloxypropylsilane | 10.0 | — | — |
| 2 | KF56*45) | 5.0 | — | — |
| 3 | Squalan | 4.0 | — | — |
| 4 | Silicone resin | 1.0 | — | — |
| 5 | Glyceryl dioleate | 2.0 | — | — |
| 6 | KF6017*33) | 2.0 | — | — |
| 7 | KF6026*36) | 4.0 | — | — |
| 8 | Dimethylpolysiloxane (viscosity 6 mm²/s) | — | — | 5.0 |
| 9 | Decamethylcyclopentasiloxane | — | — | 8.0 |
| 10 | Silicone gum lysate | — | 18.0 | — |
| 11 | Silicone network resin | — | 6.0 | — |
| 12 | Glyceryl tri-2-ethylhexanoate | — | 8.0 | — |
| 13 | Vaselline | — | 5.0 | — |
| 14 | Stearyl alcohol | — | 2.0 | — |
| 15 | Sorbitan monooleate | — | 2.0 | — |
| 16 | KF6100*38) | — | 2.0 | — |
| 17 | Copolymer of Prep. Ex. 16 | — | 4.0 | 4.0 |
| 18 | Antiseptics | q.s. | q.s. | q.s. |
| 19 | Sodium sorbitol sulfate | 2.0 | — | — |
| 20 | Sodium chondroitin sulfate | 1.0 | — | — |
| 21 | Sodium hyaluronate | 0.5 | — | — |
| 22 | Copolymer of Prep. Ex. 25 | 3.0 | — | — |
| 23 | Propylene glycol | 3.0 | — | 5.0 |
| 24 | Purified water | Balance | Balance | Balance |
| 25 | Glycerin | — | 5.0 | 3.0 |
| 26 | Sodium chloride | — | 0.5 | — |
| 27 | Stearyltrimethylammonium chloride | — | — | 1.5 |
| 28 | Hydroxyethyl cellulose | — | — | 0.2 |
| 29 | Fragrance | q.s. | q.s. | q.s. |

Silicone resin: 50% solution of a network slicone compound with a ratio [Me$_3$SiO$_{1/2}$]/[SiO$_2$] of 0.8 in Preparation Method Step A: Components 1 to 17 were heat mixed.

Step B: Components 18 to 28 were heat dissolved.

Step C: Under stirring, A was added to B slowly, emulsified, and cooled and then Component 29 was added to obtain a hair cream.

The hair creams thus obtained could be extended lightly, had non-sticky and non-greasy touch, and provided moisturized and refreshed feel, while they provided hair with gloss and smoothness. They had a good setting effect to hair.

Examples 45 to 48

Cosmetics were prepared in the following formulation.

TABLE 29

| Component | Ingredient | Blushing agent spray Ex. 45 | Hair spray Ex. 46 | Deodorant Ex. 47 | Conditioing mousse Ex. 48 |
|---|---|---|---|---|---|
| 1 | Isopropyl myristate | 0.8 | 5.0 | — | — |
| 2 | Stearyltrimethylammonium chloride | 0.05 | — | — | — |
| 3 | Alminium magnesium silicate | 0.1 | — | — | — |
| 4 | Zinc oxide treated for hydrophilicity | 3.0 | — | — | — |
| 5 | Ethanol | 25.0 | — | — | — |
| 6 | Silicone treated mica | — | 3.0 | — | — |
| 7 | Aluminum chlorohydroxy | — | 2.0 | — | — |
| 8 | Isopropylmethylphenol | — | 0.3 | — | — |
| 9 | Sorbitan sesquioleate | — | 0.2 | — | — |
| 10 | Isododecane | — | — | 6.0 | — |
| 11 | Dimethylpolysiloxane (viscosity 6 $mm^2/s$) | — | — | 2.0 | 2.0 |
| 12 | Copolymer of Prep. Ex. 14 | — | 5.0 | — | 5.0 |
| 13 | KF6017*[33] | — | — | 0.5 | — |
| 14 | KSG16*[2] | — | — | — | 0.5 |
| 15 | Glyceryl trioctanoate | — | — | — | 1.5 |
| 16 | Propylene glycol | — | — | 18.0 | — |
| 17 | Triclosan | — | — | 0.1 | — |
| 18 | Copolymer of rep. Ex. 26 | 5.0 | — | 5.0 | — |
| 19 | Glycerin | — | — | 9.0 | 3.0 |
| 20 | Stearyldimethylbenzyl-ammonium chloride | — | — | — | 0.5 |
| 21 | Polyoxyethylene hardened castor oil | — | — | — | 0.5 |
| 22 | Ethanol | — | — | — | 7.0 |
| 23 | Purified water | — | — | 29.4 | 20.0 |
| 24 | Antiseptics | q.s. | q.s. | q.s. | q.s. |
| 25 | Fragrance | q.s. | q.s. | q.s. | q.s. |
| 26 | Blowing agent | Balance | Balance | Balance | Balance |

Preparation Method

Step A: Components 1 to 15 were mixed.

Step B: Components 16 to 25 were dissolved and dispersed in A. An aerosol can was packed with the mixture and, then with Component 26 (a mixture of n-butane, isobutane, and isopropane) to obtain a blushing agent.

The spray thus obtained was glossy and very smooth and the durability of makeup was also good. It was also good in dispersibility of powder when used and made hair shiny and easy to comb.

Examples 49 to 50

Cosmetics of O/W/O type were prepared in the following formulation.

TABLE 30

| Component | Ingredient | Milky lotion Ex. 49 | Liquid foundation Ex. 50 |
|---|---|---|---|
| 1 | KSG210*[5] | 3.0 | 4.0 |
| 2 | KF6104*[39] | 1.0 | 1.0 |
| 3 | Glyceryl triisooctanoate | 14.0 | — |
| 4 | KSG43*[8] | 5.0 | — |
| 5 | Propylene glycol decanoate | — | 5.0 |
| 6 | Isorpropyl myristate | — | 5.0 |
| 7 | Copolymer of Prep. Ex. 21 | 4.0 | — |
| 8 | Copolymer of rep. Ex. 17 | — | 2.0 |
| 9 | Sucrose monostearate | 3.0 | — |
| 10 | Glycerin | 5.0 | 2.0 |
| 11 | 1,3-Butylene glycol | 5.0 | 10.0 |
| 12 | Antiseptics | q.s. | q.s. |
| 13 | Purified water | 56.0 | 52.0 |
| 14 | Pigments | 10.0 | 10.0 |
| 15 | Hydrogenated phospholipid derived from egg yolk | — | 1.0 |
| 16 | Macadamia nut oil | 2.0 | — |
| 17 | Cetyl alcohol | 2.0 | — |
| 18 | Fragrance | q.s. | q.s. |
| 19 | Squalan | 5.0 | 5.0 |
| 20 | Cetyl alcohol | — | 5.0 |

Preparation Method

Step A: Components 1 to 8 were mixed homogeneously.

Step B: Components 9 to 15 were heat mixed and made homogeneous

Step C: Components 16 to 20 were heat mixed.

Step D: C was added to B under stirring to emulsify and cooled.

Step E: D was added to A under stirring to emulsify.

The O/W/O type cosmetics thus obtained had non-sticky and non-greasy touch and transparent feel and good durability. They did not change with temperature or with time and exhibited very good sensory properties and good stability.

Examples 51 to 52

Cream cosmetics of W/O/W type were prepared in the following formulation.

TABLE 31

| Component | Ingredient | Ex. 51 | Ex. 52 |
|---|---|---|---|
| 1 | Cetyl isooctanoate | 5.0 | 2.0 |
| 2 | KSG210*5) | 6.0 | — |
| 3 | Copolymer of Prep. Ex. 8 | 0.5 | 1.0 |
| 4 | Decamethylcyclopentasiloxane | 4.5 | 1.0 |
| 5 | Methylglucose dioleate | 1.5 | 1.5 |
| 6 | Isohexadecane | 3.5 | — |
| 7 | KSG340*13) | — | 6.0 |
| 8 | Isododecane | — | 3.0 |
| 9 | Squalan | — | 6.5 |
| 10 | Magnesium sulfate | 0.5 | 0.5 |
| 11 | Propylene glycol | 5.0 | 5.0 |
| 12 | Purified water | Balance | Balance |
| 13 | Cetyl alcohol | 1.0 | 1.0 |
| 14 | PEG-10 soya seterol | 2.0 | 2.0 |
| 15 | Antiseptics | q.s. | q.s. |
| 16 | Purified water | 31.0 | 31.0 |
| 17 | Fragrance | q.s. | q.s. |

Preparation Method
Step A: Components 10 to 12 were mixed homogeneously.
Step B: Components 1 to 9 were mixed, and added to A to emulsify.
Step C: Components 13 to 16 were mixed, and B was added to the mixture under stirring to emulsify.
Step D: Component 17 was added to C and the mixture was made homogeneous.

The W/O/W type cosmetics thus obtained had non-sticky and non-greasy touch and the makeup durability was good. They did not change with temperature or with time and had very good sensory properties and good stability.

Examples 53 to 54

Antiperspirants were prepared in the following formulation.

Preparation Method of Example 53

Step A: Components 1 to 8 were mixed.

Step B: Components 9 and 16 were added to A and dispersed homogeneously.

Preparation Method of Example 54

Step A: Components 10 to 14 were mixed.

Step B: Components 15 was dissolved in Component 16.

Step C: Under stirring, B was added to A slowly and emulsified to obtain an antiperspirant.

The antiperspirants thus obtained could be extended lightly, had a non-sticky and non-greasy touch, did not leave too much white powdery residue, and gave refreshed feel to the users. They did not change with temperature or with time and stability was good.

Examples 55 to 59

Washing compositions were prepared in the following formulation.

TABLE 32

| Component | Ingredient | Roll-on type Ex. 53 | Emulsion type Ex. 54 |
|---|---|---|---|
| 1 | KSG210*5) | 10.0 | — |
| 2 | Dimethylpolysiloxane (viscosity 6 mm$^2$/s) | 10.0 | — |
| 3 | KSG15*1) | 14.3 | — |
| 4 | Decamethylcyclopentasiloxane | 30.0 | — |
| 5 | Copolymer of Prep. Ex. 20 | 10.5 | — |
| 6 | organic modified bentonite | 0.2 | — |
| 7 | Aluminum zirconium tetrachlorohydrate | 20.0 | — |
| 8 | Silicone treated zinc oxide | 5.0 | — |
| 9 | Fragrance | q.s. | — |
| 10 | Hexadimethyldisiloxane | — | 20.0 |
| 11 | Isododecane | — | 10.0 |
| 12 | Copolymer of Prep. Ex.XX | — | 2.0 |
| 13 | KF6026*36) | — | 1.0 |
| 14 | POE(20 mol) Sorbitan monooleate | — | 0.5 |
| 15 | Glycine salt of aluminium zirconium tetrachlorohydrate | — | 20.0 |
| 16 | Purified water | Balance | Balance |

TABLE 33

| Component | Ingredient | Cleansing agent Ex. 55 | Face-wash Ex. 56 | Makeup remover Ex. 57 | Hair make remover Ex. 58 | Face-wash Ex. 59 |
|---|---|---|---|---|---|---|
| 1 | Tetrakistrimethylsiloxysilane | — | — | 20.0 | — | 5.0 |
| 2 | Isododecane | — | — | — | 20.0 | — |
| 3 | Copolymer of Prep. Ex. 22 | 2.0 | 5.0 | 1.0 | 5.0 | 5.0 |
| 4 | Decamethylcyclopentasiloxane | 10.0 | 10.0 | — | — | — |
| 5 | POE(10 mol)sorbitan monolaurate | 30.0 | 5.0 | 10.0 | — | — |
| 6 | POE (15 mol) isocetylether | — | — | — | 10.0 | — |
| 7 | POE (6 mol) lauryl ether | — | — | — | — | 5.0 |
| 8 | Sodium chloride | 1.0 | — | — | 0.5 | — |
| 9 | KF6011[31] | 18.0 | 15.0 | — | — | — |
| 10 | Ethanol | — | 10.0 | — | — | 10.0 |
| 11 | Glycerin | — | 2.0 | 5.0 | 10.0 | — |
| 12 | Lauryl dimethyl amineoxide | — | — | — | — | 2.0 |
| 13 | Dipropylene glycol | — | 3.0 | — | — | 3.0 |
| 14 | 1,3-Butylene glycol | — | — | — | 10.0 | — |
| 15 | Sodium glutamate | — | 0.5 | — | — | — |
| 16 | Sorbitol | — | — | 10.0 | — | — |
| 17 | Carrageenan | — | — | 0.5 | 0.5 | — |
| 18 | Antiseptics | q.s. | q.s. | q.s. | q.s. | q.s. |
| 19 | Sodium citrate | — | — | 0.5 | — | — |
| 20 | Purified water | Balance | Balance | Balance | Balance | Balance |
| 21 | Fragrance | q.s. | q.s. | q.s. | q.s. | q.s. |

Preparation Method

Step A: Components 1 to 4 were dissolved homogeneously.

Step B: Components 5 to 21 were dissolved homogeneously.

Step C: A was added to B under stirring and dispersed homogeneously.

The washing compositions thus obtained were quickly blended with smear, such as lipstick, foundation, and setting agent for hair. Smear removing ability was very good. The removing agents could be extended lightly and the skin condition after using was also very good.

Examples 60 to 61

Cosmetics of polyalcohol in oil type were prepared in the following formulation.

TABLE 34

| Component | Ingredient | Cream Ex. 60 | Solid cheek rouge Ex. 61 |
|---|---|---|---|
| 1 | KSG15[1] | 25.0 | 5.0 |
| 2 | Tristrimethylsiloxysilane | 15.0 | — |
| 3 | Decamethylcyclopentasiloxane | — | 10.0 |
| 4 | Dimethylpolysiloxane (viscosity 6 mm$^2$/s) | 7.0 | 14.8 |
| 5 | Cetyl isooctanoate | — | 15.0 |
| 6 | Paffin wax (mp: 80 degrees C) | — | 12.0 |
| 7 | KF6017[33] | 3.0 | 3.0 |
| 8 | Copolymer of Prep. Ex. 24 | 5.0 | 3.0 |
| 9 | Dimethyldistearyl mmonium hectorite | 2.0 | 0.2 |
| 10 | Fragrance | q.s. | q.s. |
| 11 | Powder treated for hydrophobicity | — | 25.0 |
| 12 | Antiseptics | q.s. | q.s. |
| 13 | Sodium chloride | 0.1 | — |
| 14 | 1,3-Butylene glycol | Balance | Balance |

Preparation Method

Step A: Components 1 to 11 were mixed homogeneously.

Step B: Components 12 to 14 were mixed homogeneously.

Step C: Under stirring, B was added to A and emulsified homogeneously.

The emulsified cosmetics of polyalcohol in non-aqueous oil type thus obtained could be extended lightly and had non-sticky and non-greasy touch. The skin condition after using was moisturized and the stability of the cosmetics were good.

Examples 62 to 64

Creamy cosmetics were prepared in the following formulation.

TABLE 35

| Component | Ingredient | Lipstick Ex. 62 | Cleansing Ex. 63 | Foundation Ex. 64 |
|---|---|---|---|---|
| 1 | Rheopearl TT[48] | 9.0 | — | — |
| 2 | Glyceryl triisooctanoate | 22.0 | — | 4.0 |
| 3 | Bentonite | 0.7 | — | — |
| 4 | Copolymer of Prep. Ex. 9 | 1.5 | 3.0 | — |
| 5 | Copolymer of Prep. Ex. 16 | — | — | 0.5 |
| 6 | Tetrakistrimethylsiloxysilane | 42.0 | — | 6.0 |
| 7 | Dimethylpolysiloxane (viscosity 20 mm$^2$/s) | — | 5.0 | 5.0 |
| 8 | Methylphenylpolysiloxane | — | 5.0 | — |
| 9 | Liquid paraffin | — | 8.0 | — |
| 10 | KSG43[8] | — | 2.0 | — |
| 11 | Jojoba oil | — | 2.0 | — |
| 12 | KF6105[40] | — | 2.5 | — |
| 13 | KF6017[33] | — | 0.5 | — |
| 14 | Aluminum monostearate | — | 0.2 | — |
| 15 | Pigment | q.s. | — | 8.0 |
| 16 | KSG210[5] | — | — | 5.0 |
| 17 | KSP200[26] | — | — | 2.5 |
| 18 | KP575[23] | — | — | 5.0 |
| 19 | Antiseptics | q.s. | q.s. | q.s. |
| 20 | 1,3-Butylene glycol | 5.0 | — | 5.0 |
| 21 | Sodium chloride | 0.5 | — | — |
| 22 | Purified water | 19.3 | 60.0 | 59.3 |
| 23 | Aluminum chloride | — | 1.0 | — |
| 24 | Glycerin | — | 10.0 | — |
| 25 | Sodium citrate | — | — | 0.2 |
| 26 | Fragrance | q.s. | q.s. | q.s. |

Preparation Method

Step A: Components 1 to 18 were mixed homogeneously.
Step B: Components 19 to 26 were mixed and heated.
Step C: B was added to A and emulsified.

The W/O type creamy lipstick of Example 62 had a good makeup durability. It could be extended lightly and had non-sticky and non-greasy touch.

The cleansing cream of Example 63 had fine texture and could be extended lightly. The cream had non-sticky and non-greasy touch and provided moisturized and refreshed feel, while the cleansing ability was also high. They did not change with temperature or with time and had a good stability.

The cream foundation of Example 64 was non-sticky and could be extended lightly. The cream foundation was good in adhesion feel, affinity, and mat finish.

Examples 65 to 67

Eye shadows were prepared in the following formulation.

Preparation Method

A: Components 1 to 10 were mixed, and Components 11 to 19 were added and dispersed homogeneously.

B: Components 20 to 26 were dissolved homogeneously.

C: Under stirring, A was added to B slowly and emulsified to obtain an eye shadow.

The eye shadows thus obtained could be extended lightly, had non-greasy and non-powdery touch, and provided moisturized and refreshed feel, while they were good in water resistance, water repellency, sweat resistance, and makeup durability. They did not come of f easily nor change with temperature or with time and the stability was good.

Examples 68 to 70

Foundations were prepared in the following formulation.

TABLE 36

| Component | Ingredient | Ex. 65 | Ex. 66 | Ex. 67 |
|---|---|---|---|---|
| 1 | Decamethylcyclopentasiloxane | 15.0 | — | — |
| 2 | Dimethylpolysiloxane (viscosity 6 mm$^2$/s) | 10.0 | — | 4.0 |
| 3 | Copolymer of Prep. Ex. 17 | 5.0 | 5.0 | 5.0 |
| 4 | KF6009*[30] | 2.0 | — | — |
| 5 | PEG(10)lauryl ether | 0.5 | — | — |
| 6 | KP545*[20] | — | 10.0 | — |
| 7 | KP561P*[21] | — | 2.0 | — |
| 8 | KF6105*[40] | — | 1.5 | — |
| 9 | Bentone 38*[52] | — | 1.2 | — |
| 10 | Cetyl isooctanoate | — | 3.0 | — |
| 11 | Silicone treated chromium oxide | 6.2 | 6.5 | 5.0 |
| 12 | Silicone treated*[)] ultramarine blue | 4.0 | 4.0 | 4.0 |
| 13 | Silicone treated*[)] titanium-coated mica | 6.0 | 6.0 | 5.0 |
| 14 | Nylon powder | — | 3.0 | — |
| 15 | Talc | — | 4.0 | Balance |
| 16 | Sericite | — | — | 40.0 |
| 17 | Mica | — | — | 10.0 |
| 18 | Fine particle of titanium oxide | — | — | 15.0 |
| 19 | Magnesium stearate | — | — | 3.0 |
| 20 | Octyldodecanol | — | — | 3.0 |
| 21 | Sodium chloride | 2.0 | — | — |
| 22 | Propylene glycol | 8.0 | — | — |
| 23 | Antiseptics | q.s. | q.s. | — |
| 24 | Fragrance | q.s. | q.s. | — |
| 25 | Purified water | Balance | Balance | — |
| 26 | Ethanol | — | 5.0 | — |

*[)]Silicone treated: 3% of methylhydrogenpolysiloxane relative to the powder was added and then heat treated.

TABLE 37

| Component | Ingredient | Emulsion type Ex. 68 | Emulsified liquid type Ex. 69 | Emulsified liquid type Ex. 70 |
|---|---|---|---|---|
| 1 | Decamethylcyclopentasiloxane | 30.0 | 16.0 | 21.6 |
| 2 | Dimethylpolysiloxane (viscosity 6 mm$^2$/s) | 5.0 | 4.0 | 6.5 |
| 3 | Tristrimethylsiloxysilane | 10.0 | — | — |
| 4 | Copolymer of Prep. Ex. 17 | 5.0 | 4.0 | 0.5 |
| 5 | Octyl paramethoxycinnamate | — | 3.0 | — |
| 6 | 12-hydroxystearic acid | — | 1.0 | — |
| 7 | FL-5*[53] | — | 15.0 | — |
| 8 | FPD6131*[54] | — | 5.0 | — |
| 9 | KSP101*[25] | — | 3.0 | — |
| 10 | KSG15*[1] | — | — | 5.0 |

TABLE 37-continued

| Component | Ingredient | Emulsion type Ex. 68 | Emulsified liquid type Ex. 69 | Emulsified liquid type Ex. 70 |
|---|---|---|---|---|
| 11 | KF6028*[37] | — | — | 1.0 |
| 12 | Bentone38*[52] | — | — | 1.2 |
| 13 | Glyceryl trioctanoate | — | — | 5.0 |
| 14 | KP575*[23] | — | — | 1.5 |
| 15 | KSG210*[5] | 1.5 | — | 3.0 |
| 16 | KF6017*[33] | 0.5 | — | — |
| 17 | Octadecyldimethylammonium modified montmorillonite | 4.0 | — | — |
| 18 | Titanium oxide treated for hydrophobicity*) | 10.0 | — | — |
| 19 | Talc treated for hydrophobicity*) | 6.0 | — | — |
| 20 | Mica treated for hydrophobicity*) | 6.0 | — | — |
| 21 | Colcothar treated for hydrophobicity*) | 1.6 | — | — |
| 22 | Iron oxide yellow treated for hydrophobicity*) | 0.7 | — | — |
| 23 | Iron oxide black treated for hydrophobicity*) | 0.2 | — | — |
| 24 | Fine particle of titanium oxide treated with fluorinated compound**) | — | 8.0 | — |
| 25 | Mica titanium treated with fluorinated compound**) | — | 1.0 | — |
| 26 | Titanium oxide treated with fluorinated compound**) | — | 5.0 | — |
| 27 | Colcothar treated with fluorinated compound**) | — | 0.9 | — |
| 28 | Iron oxide yellow treated with fluorinated compound**) | — | 2.0 | — |
| 29 | Iron oxide black treated with fluorinated compound**) | — | 1.0 | — |
| 30 | KF9909 treated pigments | — | 10.0 | — |
| 31 | Dipropylene glycol | 5.0 | — | 5.0 |
| 32 | Methyl para-oxybenzoate | 0.3 | — | — |
| 33 | 2-amino-2-methyl-1,3-propanediol | 0.2 | — | — |
| 34 | Hydrochloric acid | 0.1 | — | — |
| 35 | Purified water | Balance | Balance | Balance |
| 36 | Ethanol | — | 15.0 | — |
| 37 | Glycerin | — | 3.0 | — |
| 38 | Magnesium sulfate | — | 1.0 | — |
| 39 | Sodium citrate | — | — | 0.2 |
| 40 | Antiseptics | q.s. | q.s. | q.s. |
| 41 | Fragrance | q.s. | q.s. | q.s. |

*)Treated for hydophobicity: 2% of methylhydrogenpolysiloxane relative to the powder was added and then heat treated.
**)Treated with fluorinated compound: coated with 5% of ethanolamine salt of perfouoroalkylethyl phosphoric acid relative to the powder.

Preparation Method

Step A: Components 1 to 17 were mixed homogeneously and Components 18 to 30 were added and dispersed homogeneously.

Step B: Components 31 to 40 were heat dissolved.

Step C: Under stirring, B was added to A slowly, emulsified, cooled and then Component 41 was added to obtain a foundation.

The foundations thus obtained had fine texture and could be extended lightly. The foundations had non-sticky and non-greasy touch and provided moisturized and refreshed feel and mat finish, while the makeup durability was good. They did not change with temperature or with time and stability was good.

Examples 71 to 73

Creams were prepared in the following formulation.

TABLE 38

| Component | Ingredient | Moisturizing cream Ex. 71 | Hand cream Ex. 72 | Wrinkle hiding cream Ex. 73 |
|---|---|---|---|---|
| 1 | Decamethylcyclopentasiloxane | 10.0 | 30.0 | 13.0 |
| 2 | Liquid paraffin | — | 10.0 | — |
| 3 | KSG16*[2] | 3.0 | — | 15.0 |
| 4 | KSG15*[1] | — | — | 55.0 |
| 5 | Copolymer of Prep. Ex. 8 | 2.0 | 5.0 | 2.0 |
| 6 | KSG310*[10] | 5.0 | — | — |
| 7 | Pentaerythritol tetra-2-ethylhexanoate | 3.0 | — | — |
| 8 | Cetyl 2-ethylhexanoate | 5.0 | — | — |
| 9 | KSG210*[5] | — | — | 5.0 |

TABLE 38-continued

| Component | Ingredient | Moisturizing cream Ex. 71 | Hand cream Ex. 72 | Wrinkle hiding cream Ex. 73 |
|---|---|---|---|---|
| 10 | KF6017*[33] | 1.0 | 4.0 | — |
| 11 | KSP300*[27] | 2.5 | — | — |
| 12 | KSP100*[24] | — | — | 8.0 |
| 13 | KMP590*[28] | — | — | 2.0 |
| 14 | AerosilR972*[56] | 2.0 | — | — |
| 15 | Zinc stearate | 2.0 | — | — |
| 16 | Vitamin E acetate | 3.0 | 0.1 | — |
| 17 | Gummy amino modified silicone | — | 15.0 | — |
| 18 | Distearyldimethylammonium chloride | — | 0.8 | — |
| 19 | Polyethylene glycol 400 | 1.0 | — | — |
| 20 | Polyethylene glycol 4000 | — | 1.0 | — |
| 21 | Sodium lactate | 1.0 | — | — |
| 22 | 1,3-Butylene glycol | 5.0 | — | — |
| 23 | Glycerin | — | 10.0 | — |
| 24 | Aluminum magnesium silicate | — | 1.2 | — |
| 25 | Purified water | Balance | Balance | Balance |
| 26 | Antiseptics | q.s. | q.s. | q.s. |
| 27 | Fragrance | q.s. | q.s. | q.s. |

Gummy amino modified silicone: aminopropyl modified gummy dimethicone (amine equivalent: 70,000 g/mol; viscosity: 30,000,000 mm$^2$/s)

Preparation Method

Step A: Components 1 to 16 were mixed homogeneously.

Step B: Components 18 to 26 were dissolved homogeneously.

Step C: B was added to A slowly, emulsified, and cooled. Then Component 27 was added to obtain a moisturizing cream.

The moisturizing creams thus obtained could be extended lightly, had non-sticky touch, and provided hydrated and refreshed feel. They did not change with temperature or with time and the stability was very good. They provided mat finish without greasy shine.

Examples 74 to 76

Cosmetics were prepared in the following formulation.

TABLE 39

| Component | Ingredient | Serum Ex. 74 | Treatment gel Ex. 75 | Packing agent of leave-on type Ex. 76 |
|---|---|---|---|---|
| 1 | Decamethylcyclopentasiloxane | 12.0 | — | — |
| 2 | Glyceryl triisooctanoate | 10.0 | 3.0 | — |
| 3 | Dimethylpolysiloxane (viscosity 6 mm$^2$/s) | — | — | 3.0 |
| 4 | KF6017*[33] | 0.2 | — | — |
| 5 | KSG21*[4] | 2.0 | — | — |
| 6 | Copolymer of Prep. Ex. 9 | 2.0 | 5.0 | 3.0 |
| 7 | Ethanol | — | 15.0 | — |
| 8 | KF6018*[34] | — | 0.5 | 2.0 |
| 9 | KF7002*[58] | — | 2.0 | — |
| 10 | KSP100*[24] | — | 8.0 | — |
| 11 | Kaolin | — | — | 30.0 |
| 12 | Glycerin | 10.0 | — | 10.0 |
| 13 | Magnesium ascorbate phosphate | 3.0 | — | — |
| 14 | Copolymer of Prep. Ex. 25 | 1.0 | 1.0 | 1.0 |
| 15 | Sodium chloride | 2.0 | — | — |
| 16 | Antiseptics | q.s. | q.s. | q.s. |
| 17 | Purified water | Balance | Balance | Balance |
| 18 | Carboxyvinyl polymer (1% aq. sol.) | — | 20.0 | 20.0 |
| 19 | Triethanolamine | — | 0.2 | 0.2 |
| 20 | 1,3-Butylene glycol | — | — | 10.0 |
| 21 | Fragrance | q.s. | q.s. | q.s. |

Preparation Method

Step A: Components 1 to 11 were mixed homogeneously.

Step B: Components 12 to 20 were dissolved homogeneously.

Step C: Under stirring, B was added to A, emulsified, and cooled. Component 21 was added to obtain a serum.

The cosmetics thus obtained could be extended lightly, had non-sticky touch, and provided moisturized and refreshed finish. They did not change with temperature or with time and stability was very good.

Examples 77 to 80

Cosmetics were prepared in the following formulation.

TABLE 40

| Component | Ingredient | Powder foundation Ex. 77 | Powder eyebrow Ex. 78 | Oil-based foundation Ex. 79 | Mascara Ex. 80 |
|---|---|---|---|---|---|
| 1 | Vaselline | 2.5 | 2.5 | — | — |
| 2 | Squalan | 3.0 | — | — | — |
| 3 | Dimethylpolysiloxane (viscosity 6 mm²/s) | — | 1.5 | — | — |
| 4 | Decamethylcyclopentasiloxane | — | — | 14.0 | — |
| 5 | KP562P*[22] | — | — | — | 10.0 |
| 6 | Tristrimethylsiloxypropylsilane | — | — | — | 10.0 |
| 7 | Rheopearl TT*[48] | — | — | 6.0 | 8.0 |
| 8 | Ceresin | — | — | 7.0 | 7.0 |
| 9 | Polyethylene wax | — | — | — | 4.0 |
| 10 | Lecithin | — | — | — | 0.5 |
| 11 | Isododecane | — | — | — | 20.0 |
| 12 | Copolymer of Prep. Ex. 10 | 0.5 | 0.5 | 4.0 | 4.0 |
| 13 | Glyceryl trioctanoate | 2.0 | 4.0 | — | — |
| 14 | Liquid paraffin | — | — | 20.0 | 18.0 |
| 15 | KF6105*[40] | — | — | 6.0 | — |
| 16 | Silicone treated mica | 40.0 | 40.0 | 10.0 | — |
| 17 | Silicone treated talc | Balance | Balance | — | Balance |
| 18 | Silicone treated fine particle of titanium oxide | 5.0 | 10.0 | Balance | — |
| 19 | Silicone treated barium sulfate | 10.0 | 15.0 | — | — |
| 20 | Silicone treated iron oxide black | — | — | — | 5.0 |
| 21 | Aerosil RY200*[57] | — | — | — | 3.5 |
| 22 | Mica titanium | — | — | 3.0 | — |
| 23 | KSP300*[27] | 2.0 | — | — | — |
| 24 | KSP100*[24] | — | 1.5 | — | — |
| 25 | KMP590*[28] | 2.5 | 2.5 | — | — |
| 26 | Antiseptics | q.s. | q.s. | q.s. | — |
| 27 | Fragrance | q.s. | q.s. | q.s. | — |

Preparation Method

Step A: Components 16 to 25 were mixed homogeneously.

Step B: Components 1 to 15 and Component 26 were mixed homogeneously. The mixture was added to A and made homogeneous.

Step C: Component 27 was added to B and the mixture was poured into a container, optionally followed by press forming, to obtain a cosmetic.

The cosmetics thus obtained could be extended lightly, had non-sticky touch, and provided good affinity and glossy finish.

Examples 81 to 83

Eyeliners were prepared in the following formulation.

Preparation Method

Step A: Components 1 to 11 were mixed and dispersed homogeneously.

Step B: Components 12 to 16 were mixed.

Step C: B was added to A slowly, emulsified, and cooled to obtain an eyeliner.

The eyeliners thus obtained could be extended lightly and were easy to draw with. They provided refreshed finish and non-sticky touch. They did not change with temperature or with time. They were good in sensory properties, stability, and both water and sweat resistance. The makeup durability was also good.

TABLE 41

| Component | Ingredient | Ex. 81 | Ex. 82 | Ex. 83 |
|---|---|---|---|---|
| 1 | Decamethylcyclopentasiloxane | 53.5 | — | — |
| 2 | Tristrimethylsiloxypropylsilane | — | 20.0 | — |
| 3 | Dimethylpolysiloxane (viscosity 6 mm²/s) | — | 5.0 | 5.0 |
| 4 | KF6017*[33] | 3.0 | — | 1.0 |
| 5 | KF7312J*[29] | 5.0 | — | — |
| 6 | Vitamin E acetate | — | 0.2 | — |
| 7 | Jojoba oil | — | 2.0 | 2.0 |
| 8 | Bentonite | — | 3.0 | — |
| 9 | Copolymer of Prep. Ex. 13 | 10.0 | 2.0 | 22.0 |
| 10 | Dimethyldistearylammonium hectorite | 3.0 | — | — |
| 11 | Silicone treated*) iron oxide black | 10.0 | 20.0 | 20.0 |
| 12 | Ethanol | — | 10.0 | 5.0 |
| 13 | 1,3-Butylene glycol | 5.0 | 10.0 | — |
| 14 | Sodium sulfate | 0.5 | — | — |
| 15 | Antiseptics | q.s. | q.s. | q.s. |
| 16 | Purified water | Balance | Balance | Balance |

*)Silicone treated iron oxide black: 2% of methylhydrogenpolysiloxane relative to iron oxide black was added, and then heat treated.

Examples 84 to 88

W/O creams were prepared in the following formulation.

TABLE 42

| Component | Ingredient | Ex. 84 | Ex. 85 | Ex. 86 | Ex. 87 | Ex. 88 |
|---|---|---|---|---|---|---|
| 1 | Decamethylcyclopentasiloxane | 15.0 | — | — | — | 18.0 |
| 2 | Glyceryl trioctanoate | 10.0 | — | — | — | — |
| 3 | Dimethylpolysiloxane (viscosity 6 mm$^2$/s) | — | 10.0 | — | — | — |
| 4 | Liquid paraffin | — | 5.0 | 5.0 | — | — |
| 5 | Tristrimethylsiloxypropylsilane | — | — | — | 18.0 | — |
| 6 | KF56*[45] | — | — | — | 5.0 | — |
| 7 | KF6017*[33] | 1.5 | 3.0 | — | 1.0 | 1.4 |
| 8 | KF6104*[39] | 4.0 | — | — | — | — |
| 9 | KF6105*[40] | — | — | — | — | 2.5 |
| 10 | KSG340*[13] | — | 5.0 | — | — | — |
| 11 | KSG310*[10] | — | — | 1.0 | — | — |
| 12 | Dextrin ester of aliphatic acid | — | — | — | 1.0 | — |
| 13 | Copolymer of Prep. Ex. 14 | 5.0 | — | — | 2.0 | — |
| 14 | Copolymer of Prep. Ex. 16 | — | 5.0 | — | — | 2.0 |
| 15 | Copolymer of Prep. Ex. 19 | — | — | 20.0 | — | — |
| 16 | Polypropylene glycol (3) myristyl ether | — | — | — | — | 0.5 |
| 17 | Phenyldimethylstearylammonium chloride | 1.0 | — | — | — | — |
| 18 | Antiseptics | q.s. | q.s. | q.s. | q.s. | q.s. |
| 19 | Fine particle of titanium oxide treated for hydrophobicity | — | — | — | — | 1.0 |
| 20 | Dipropylene glycol | 10.0 | — | 5.0 | — | — |
| 21 | 1,3-Butylene glycol | — | 5.0 | — | — | — |
| 22 | Glycerin | — | — | 5.0 | 5.0 | 3.0 |
| 23 | Multitol | 10.0 | — | — | — | — |
| 24 | 70% Sorbitol | — | — | — | — | 5.0 |
| 25 | Saponite | 1.5 | — | — | — | — |
| 26 | Purified water | Balance | Balance | Balance | Balance | Balance |
| 27 | Sodium citrate | — | 2.0 | — | — | — |
| 28 | Sodium chloride | — | — | — | 1.0 | 0.6 |
| 29 | Citric acid | — | — | — | — | 25.0 |
| 30 | 32% Aqueous ammonium | — | — | — | — | 4.5 |
| 31 | Magnesium L-ascorbate phosphate ester | — | — | 3.0 | — | — |
| 32 | Fragrance | q.s. | q.s. | q.s. | q.s. | q.s. |

Preparation Method

Step A: Components 1 to 19 were heat mixed.
Step B: Components 20 to 31 were heat dissolved.
Step C: Under stirring, B was added to A, emulsified, and cooled. Component 32 was added to obtain a cream.

The creams thus obtained could be extended lightly, had non-sticky and non-greasy touch, and provided moisturized and refreshed feel, while they provided good water resistance and good makeup durability. They did not change with temperature or with time and were good in stability.

Examples 89 to 93

W/O creams were prepared in the following formulation.

TABLE 43

| Component | Ingredient | Hand cream Ex. 89 | Sun block cream Ex. 90 | Lip cream Ex. 91 | Sun block cream Ex. 92 | Eye wrinkle cream Ex. 93 |
|---|---|---|---|---|---|---|
| 1 | Decamethylcyclopentasiloxane | — | — | 40.0 | — | — |
| 2 | squalan | — | — | 10.0 | — | — |
| 3 | KF56*[45] | — | — | — | 18.0 | — |
| 4 | Lanolin | — | — | 2.0 | — | — |
| 5 | Liquid paraffin | 10.0 | 20.0 | — | 1.5 | — |
| 6 | Silicone resin lysate | 5.0 | — | — | — | 5.0 |
| 7 | Tristrimethylsiloxymethylsilane | — | — | — | — | 20.0 |
| 8 | Microcrystalline wax | — | — | 3.0 | — | — |
| 9 | KF6017*[33] | 1.9 | 1.9 | 3.0 | — | — |
| 10 | KF6009*[30] | — | — | — | 4.0 | — |
| 11 | KF6104*[39] | — | — | — | — | 5.0 |
| 12 | Dibutylamide of lauroylglutamic acid | — | — | 5.0 | — | — |
| 13 | KSG41*[6] | — | — | — | 5.0 | — |
| 14 | KSG42*[7] | — | — | 10.0 | — | — |
| 15 | KSG320*[11] | — | 4.0 | — | — | — |
| 16 | KSG310*[10] | 4.0 | — | — | — | — |
| 17 | Copolymer of Prep. Ex. 15 | 12.0 | — | — | 2.0 | — |
| 18 | Copolymer of Prep. Ex. 6 | — | 10.0 | — | — | 2.0 |

TABLE 43-continued

| Component | Ingredient | Hand cream Ex. 89 | Sun block cream Ex. 90 | Lip cream Ex. 91 | Sun block cream Ex. 92 | Eye wrinkle cream Ex. 93 |
|---|---|---|---|---|---|---|
| 19 | Vitamin E acetate | 0.1 | 0.1 | — | — | — |
| 20 | 4-t-butyl-4'-methoxybenzoylmethane | — | 7.0 | — | — | — |
| 21 | Octyl paramethoxycinnamate | — | — | — | 5.0 | — |
| 22 | Distearyldimethylammonium chloride | 0.8 | 0.8 | — | — | — |
| 23 | Antiseptics | q.s. | q.s. | q.s. | q.s. | q.s. |
| 24 | Sodium lactate | — | — | 0.3 | — | 1.0 |
| 25 | Sodium chloride | — | — | — | 1.0 | — |
| 26 | Sodium chondroitin sulfate | — | — | — | — | 2.0 |
| 27 | Ethanol | — | 1.0 | — | — | — |
| 28 | 1,3-Butylene glycol | — | — | — | 4.0 | — |
| 29 | Glycerin | 10.0 | — | 5.0 | — | 50.0 |
| 30 | Aluminum magnesium silicate | 1.2 | 1.2 | — | — | — |
| 31 | Sorbitol | — | — | 0.5 | — | — |
| 32 | Purified water | Balance | Balance | Balance | Balance | Balance |
| 33 | Sodium L-glutamate | — | — | 0.3 | — | — |
| 34 | Sodium hyaluronate | — | — | 0.1 | — | — |
| 35 | Red 202 | — | — | q.s. | — | — |
| 36 | Fragrance | q.s. | q.s. | q.s. | q.s. | q.s. |

Silicone resin lysate: lysate of 50% of a network silicone compound with a ratio $[Me_3SiO_{1/2}]/[SiO_2]$ of 1.15 and 50% of M3T-C3

Preparation Method

Step A: Components 1 to 21 were heat mixed.
Step B: Components 22 to 35 were heat dissolved.
Step C: Under stirring, B was added to A slowly, emulsified, and cooled. Then Component 36 was added to obtain a cream.

The creams thus obtained could be extended lightly, had non-sticky and non-greasy touch, and provided moisturized and refreshed feel, while they were good in water resistance, water repellency, and makeup durability. They did not change with temperature or with time and stability was also good.

Examples 94 to 96

W/O creams were prepared in the following formulation.

TABLE 44

| Component | Ingredient | Suncut cream Ex. 94 | Moisturizing cream Ex. 95 | Whitening cream for day time Ex. 96 |
|---|---|---|---|---|
| 1 | Decamethylcyclopentasiloxane | — | 10.0 | — |
| 2 | Glyceryl triisooctanoate | 5.0 | — | — |
| 3 | KF56*[45] | — | — | 5.0 |
| 5 | Isododecane | — | 5.0 | — |
| 6 | KP545*[20] | 12.0 | — | — |
| 7 | Tristrimethylsiloxymethylsilane | 15.0 | 3.0 | 22.0 |
| 8 | KF6017*[33] | — | — | 1.0 |
| 9 | KF6009*[30] | — | 2.0 | — |
| 10 | KF6104*[39] | 1.0 | — | — |
| 11 | KSG21*[4] | 5.0 | — | — |
| 12 | KMP590*[28] | — | 2.5 | — |
| 13 | Aerosil R972*[56] | — | 2.0 | — |
| 14 | KF7002*[58] | — | 8.0 | — |
| 15 | Zinc oxide treated for hydrophilicity | 20.0 | — | — |
| 16 | Zinc stearate | — | 2.0 | — |
| 17 | Copolymer of Prep. Ex. 7 | 2.5 | — | — |
| 18 | Copolymer of Prep. Ex. 12 | — | 10.0 | — |
| 19 | Copolymer of Prep. Ex. 13 | — | — | 3.0 |
| 20 | Vitamin E acetate | — | 3.0 | — |
| 21 | Octyl paramethoxycinnamate | 6.0 | — | — |
| 22 | Polyethylene glycol 400 | — | 1.0 | — |
| 23 | Antiseptics | q.s. | q.s. | q.s. |
| 24 | Sodium lactate | — | 1.0 | — |
| 25 | Sodium chloride | 0.5 | — | 0.9 |
| 26 | Sodium ascorbate sulfate | — | — | 0.1 |
| 27 | Sodium ascorbate phosphate | — | — | 0.1 |
| 28 | 1,3-Butylene glycol | 2.0 | 5.0 | 10.0 |
| 29 | Glycerin | — | — | 5.0 |
| 30 | Gamma-aminobutyric acid | — | — | 0.1 |
| 31 | Apple seed kernel extract | — | — | 0.1 |
| 32 | Purified water | Balance | Balance | Balance |
| 33 | Fragrance | q.s. | q.s. | q.s. |

Preparation Method

Step A: Components 1 to 21 were heat mixed.
Step B: Components 22 to 32 were heat dissolved.
Step C: Under stirring, B was added to A slowly, emulsified, and cooled. Component 33 was added to obtain a cream.

The creams thus obtained could be extended lightly, had non-sticky and non-greasy touch, and provided moisturized and refreshed feel, while they were good in water resistance, water repellency, and makeup durability. They did not change with temperature or with time and stability was also good.

Examples 97 to 100

Foundations were prepared in the following formulation.

Step B: Components 32 to 39 were heat dissolved.
Step C: Under stirring, B was added to A slowly, emulsified, and cooled. Component 40 was added to obtain a foundation.

The emulsified foundations thus obtained were less viscous and had fine texture. They could be extended lightly, had non-sticky and non-greasy touch, and provided moisturized and refreshed feel, while they were good in makeup durability. They did not change with temperature or with time and stability was also good. Particularly, the foundation of Example 97 was of emulsified liquid type. The foundation of Example 100 was of non-fluid emulsified type, could be formed in a compact, and exhibited good usability.

TABLE 45

| Component | Ingredient | Ex. 97 | Ex. 98 | Ex. 99 | Ex. 100 |
|---|---|---|---|---|---|
| 1 | Decamethylcyclopentasiloxane | — | — | 15.0 | — |
| 2 | Liquid paraffin | — | — | 3.0 | 3.0 |
| 3 | Dimethylpolysiloxane (viscosity 6 mm$^2$/s) | 15.0 | — | — | 15.5 |
| 4 | Squalan | 4.0 | — | — | — |
| 5 | Ceresin | — | — | — | 5.5 |
| 6 | Microcrystalline wax | — | — | — | 1.0 |
| 7 | Neopentylglycol dioctanoate | 5.0 | — | — | — |
| 8 | alfa-monoisostearylglycerylether | 1.0 | — | — | — |
| 9 | KF56*[45)] | — | 18.0 | — | — |
| 10 | Sorbitan monoisostearate | — | 0.5 | — | — |
| 11 | Diglyceryl monoisostearate | — | 0.5 | — | — |
| 12 | PolypropyleneglycolDicaprylate | — | — | — | 3.0 |
| 13 | KP561*[21)] | — | 1.0 | — | — |
| 14 | KF6015*[32)] | — | — | 3.0 | — |
| 15 | Palmitic acid | — | — | 0.5 | — |
| 16 | AerosilRY200*[57)] | — | — | 5.0 | — |
| 17 | KSG710*[14)] | 1.0 | — | — | — |
| 18 | KSG310*[10)] | — | — | — | 9.0 |
| 19 | Copolymer of Prep. Ex. 22 | 5.0 | — | 5.0 | — |
| 20 | Copolymer of Prep. Ex. 18 | — | 5.0 | — | 1.0 |
| 21 | Aluminum distearate | 0.2 | — | — | — |
| 22 | Titanium oxide treated for hydrophobicity | 5.0 | 10.0 | 6.0 | 10.0 |
| 23 | Cerisite treated for hydrophobicity | 2.0 | — | 8.03 | 2.0 |
| 24 | Talc treated for hydrophobicity | 3.0 | 2.5 | — | 2.0 |
| 25 | Colcothar treated for hydrophobicity | 0.4 | 0.13 | 0.25 | 0.3 |
| 26 | Iron oxide yellow treated for hydrophobicity | 0.7 | 0.3 | 0.6 | 0.5 |
| 27 | Iron oxide black treated for hydrophobicity | 0.1 | 0.07 | 0.12 | 0.2 |
| 28 | Lecithin | — | — | — | 0.3 |
| 29 | Vitamin E acetate | — | — | 0.2 | — |
| 30 | Octyl paramethoxycinnamate | — | 3.0 | — | — |
| 31 | Sorbitol | — | 2.0 | — | — |
| 32 | Antiseptics | q.s. | q.s. | q.s. | q.s. |
| 33 | Polyoxyethylene sorbitan monooleate | — | — | — | 0.5 |
| 34 | Magnesium sulfate | 0.7 | 0.1 | 2.0 | — |
| 35 | Ethanol | — | 10.0 | — | — |
| 36 | Dipropylene glycol | — | — | 10.0 | 8.0 |
| 37 | Glycerin | 3.0 | — | — | — |
| 38 | Sodium citrate | — | — | — | 0.2 |
| 39 | Purified water | Balance | Balance | Balance | Balance |
| 40 | Fragrance | q.s. | q.s. | q.s. | q.s. |

Preparation Method

Step A: Components 1 to 20 and Components 28 to 31 were heat mixed and a homogeneous dispersion of Components 21 to 27 was added and mixed sufficiently.

Examples 101 to 104

Milky lotions were prepared in the following formulation.

TABLE 46

| Component | Ingredient | Ex. 101 | Ex. 102 | Ex. 103 | Ex. 104 |
|---|---|---|---|---|---|
| 1 | Decamethylcyclopentasiloxane | 15.0 | 20.0 | — | — |
| 2 | Octamethyltrisiloxane | — | — | 20.0 | — |
| 3 | Tetrakistrimethylsiloxysilane | — | — | — | 15.0 |
| 4 | KF56*[45)] | — | — | — | 5.0 |

TABLE 46-continued

| Component | Ingredient | Ex. 101 | Ex. 102 | Ex. 103 | Ex. 104 |
|---|---|---|---|---|---|
| 5 | Squalan | 5.0 | — | — | 5.0 |
| 6 | Neopentylglycol dioctanoate | 3.0 | — | — | — |
| 7 | alfa-monooleylglycerylether | 1.0 | — | — | — |
| 8 | Diglyceryl monoisostearate | — | 1.5 | — | — |
| 9 | Decaglyceryl pentaisostearate | — | 1.5 | — | — |
| 10 | Pentaerythritol tetra-2-ethylhexanoate | — | — | — | 5.0 |
| 11 | Sorbitan monoisostearate | — | — | 1.0 | — |
| 12 | Olive oil | — | 1.0 | — | — |
| 13 | KSG830*[17] | 1.5 | — | — | — |
| 14 | KF6017*[33] | 1.0 | 0.5 | 0.5 | 3.0 |
| 15 | Copolymer of Prep. Ex. 12 | 6.0 | — | — | 2.0 |
| 16 | Copolymer of Prep. Ex. 18 | — | 5.0 | — | — |
| 17 | Copolymer of Prep. Ex. 8 | — | — | 3.0 | — |
| 18 | Aluminum distearate | 0.2 | — | — | — |
| 19 | Rheopearl TT*[48] | 1.0 | — | — | — |
| 20 | SPD-T5*[41] | — | 7.0 | 5.0 | — |
| 21 | Octyl paramethoxycinnamate | — | — | 4.0 | — |
| 22 | SPD-Z5*[42] | — | — | 8.0 | — |
| 23 | KSP101*[25] | — | — | — | 2.0 |
| 24 | Aerosil R972*[56] | — | — | — | 0.5 |
| 25 | Magnesium sulfate | 0.7 | — | — | — |
| 26 | Glycerin | 5.0 | 5.0 | — | — |
| 27 | Sodium chloride | — | 1.5 | 2.0 | 1.0 |
| 28 | Sorbitol | — | — | 2.0 | — |
| 29 | Magnesium ascorbate phosphate | — | — | — | 1.0 |
| 30 | Polyethylene glycol 1000 | — | — | — | 1.0 |
| 31 | Propylene glycol | — | — | — | 8.0 |
| 32 | Purified water | Balance | Balance | Balance | Balance |
| 33 | Antiseptics | q.s. | q.s. | q.s. | q.s. |
| 34 | Fragrance | q.s. | q.s. | q.s. | q.s. |

Preparation Method

Step A: Components 1 to 24 were heat mixed.

Step B: Components 25 to 33 were heat dissolved.

Step C: Under stirring, B was added to A slowly, emulsified, and cooled. Component 34 was added to obtain a milky lotion.

The milky lotions thus obtained were less viscous and had fine texture. They could be extended lightly, had non-sticky and non-greasy touch, and provided moisturized and refreshed feel, while they were good in makeup durability. They did not change with temperature or with time and stability was also good.

Examples 105 to 108

Cosmetics were prepared in the following formulation.

TABLE 47

| Component | Ingredient | Transparent gel-like cosmetic Ex. 105 | Anti-perspirant Ex. 106 | Anti-perspirant Ex. 107 | After shave cream Ex. 108 |
|---|---|---|---|---|---|
| 1 | KF6100*[38] | 10.0 | — | — | — |
| 2 | Decamethylcyclopentasiloxane | — | 30.0 | 30.0 | 35.0 |
| 3 | Polyoxyethylene sorbitan monooleate(20EO) | — | — | 0.5 | — |
| 4 | Aloe extract | — | — | — | 0.1 |
| 5 | KSG210*[5] | — | 20.0 | — | — |
| 6 | KSG15*[1] | — | 20.0 | — | — |
| 7 | KF6017*[33] | — | — | — | 2.9 |
| 8 | Copolymer of Prep. Ex. 9 | 10.0 | — | — | 5.0 |
| 9 | Copolymer of Prep. Ex. 13 | — | 10.0 | 5.0 | — |
| 10 | 1,3-Butylene glycol | 10.0 | — | — | — |
| 11 | Polyethylene glycol 400 | 9.0 | — | — | 5.0 |
| 12 | 2-hydroxyoctanoic acid | 1.0 | — | — | — |
| 13 | 70% Sorbitol | 10.0 | — | — | — |
| 14 | Citric acid | q.s. | — | — | — |
| 15 | Sodium citrate | q.s. | — | — | — |
| 16 | Aluminum zirconium tetrachlorohydrex GLY | — | 20.0 | 20.0 | — |
| 17 | Sodium L-glutamate | — | — | — | 2.0 |
| 18 | Purified water | Balance | 0 | Balance | Balance |
| 19 | Antiseptics | q.s. | 0 | q.s. | q.s. |
| 20 | Fragrance | q.s. | 0 | q.s. | q.s. |

Preparation Method

Step A: Components 1 to 9 were heat mixed.

Step B: Components 10 to 20 were heat dissolved.

Step C: Under stirring, B was added to A slowly and dispersed homogeneously to obtain a cosmetic.

The cosmetics thus obtained had fine texture, could be extended lightly, had non-sticky and non-greasy touch, and provided moisturized and refreshed feel, while they were good in makeup durability. They did not change with temperature or with time and stability was also good.

Examples 109 to 111

Cosmetics of O/W type were prepared in the following formulation.

TABLE 48

| Component | Ingredient | Cream Ex. 109 | Hand cream Ex. 110 | Lotion Ex. 111 |
|---|---|---|---|---|
| 1 | Dimethylpolysiloxane (viscosity 6 mm²/s) | 4.0 | — | — |
| 2 | Decamethylcyclopentasiloxane | 16.0 | — | 14.0 |
| 3 | KP562P | — | 5.0 | — |
| 4 | Tetrakistrimethylsiloxysilane | — | 5.0 | — |
| 5 | Glyceryl triisooctanoate | — | 3.0 | — |
| 6 | Sunsphere SZ-5*[60] | 2.0 | — | — |
| 7 | Silicone treated titanium oxide fine particle | 10.0 | — | — |
| 8 | Liquid paraffin | 2.0 | — | — |
| 9 | Macadamia nut oil | 1.0 | — | — |
| 10 | Baikal skullcup extract | 1.0 | — | — |
| 11 | Gentian extract | 0.5 | — | — |
| 12 | KSG16*[2] | — | 2.0 | — |
| 13 | Vaselline | — | 5.0 | — |
| 14 | squalan | — | — | 1.5 |
| 15 | Octyl paramethoxycinnamate | — | — | 3.0 |
| 16 | Titanium TTO-S2*[59] | — | — | 2.0 |
| 17 | Copolymer of Prep. Ex. 10 | 5.0 | — | — |
| 18 | Copolymer of Prep. Ex. 24 | — | 5.0 | — |
| 19 | Copolymer of Prep. Ex. 25 | — | — | 5.0 |
| 20 | POE(5 mol) Octyldodecylether | 1.0 | — | — |
| 21 | POE(20 mol) Sorbitan monostearate | 0.5 | 1.0 | — |
| 22 | Ethanol | 5.0 | — | — |
| 23 | 1,3-Butylene glycol | 2.0 | 5.0 | 10.0 |
| 24 | Sepigel 305*[50] | — | 2.0 | — |
| 25 | Glycerin | — | 5.0 | — |
| 26 | Sodium chloride | — | — | 2.0 |
| 27 | L-Proline | — | — | 0.1 |
| 28 | 2-hydroxyoctanoic acid | — | — | 1.0 |
| 29 | 2-hydroxypuropanoic acid | — | — | 5.0 |
| 30 | Sodium hydroxide | — | — | 0.2 |
| 31 | Purified water | Balance | Balance | Balance |
| 32 | Antiseptics | q.s. | q.s. | q.s. |
| 33 | Fragrance | q.s. | q.s. | q.s. |

Baikal skullcup extract: extracted with 50% aqueous 1,3-butylene glycol
Gentian extract: extracted with 20% aqueous ethanol Preparation Method Step A: Components 1 to 19 were mixed homogeneously.
Step B: Components 20 to 33 were mixed homogeneously.
Step C: Under stirring, A was added to B slowly and emulsified to obtain a cosmetic Comparative Preparation Examples 8, Examples 112 to 113, and Comparative Example 13

A copolymer was obtained in the same manner as that in Preparation Example 1 by using 50 parts by mass of organopolysiloxane represented by Formula (10), 5 parts by mass of 2-methacryloyloxyethyl phoshorylcholine represented by Formula (11), 35 parts by mass of methyl methacrylate, 10 parts by mass of 3-methacryroyloxypropyltriethoxy silane, 120 parts by mass of ethanol, and 1 part by mass of dimetyl-2,2'-azobis(2-methylpropionate). The polymer was solid resin and the number average molecular weight reduced to polystyrene, determined by GPC, was 123,000. Powder foundations were prepared according to the prescriptions in the following table by using the resins from Preparation Examples 1 and 4 and from the above-described Comparative Preparation Examples.

TABLE 49

| Component | Ingredient | Ex. 112 | Ex. 113 | Com. Prep. 13 |
|---|---|---|---|---|
| 1 | vaselline | 3 | 3 | 3 |
| 2 | Squalan | 3 | 3 | 3 |

TABLE 49-continued

| Component | Ingredient | Ex. 112 | Ex. 113 | Com. Prep. 13 |
|---|---|---|---|---|
| 3 | Dimethylpolysiloxane (viscosity 6 mm²/s) | 1.5 | 1.5 | 1.5 |
| 4 | Copolymer of Prep. Ex. 1 | 3 | 0 | 0 |
| 5 | Copolymer of Prep. Ex. 4 | 0 | 3 | 0 |
| 6 | Copolymer of Com. Prep. Ex. 8 | 0 | 0 | 3 |
| 7 | Glyceryl trioctanoate | 2 | 2 | 2 |
| 8 | Mica | 40 | 40 | 40 |
| 9 | Talc | Balance | Balance | Balance |
| 10 | Titanium oxide fine particle | 5 | 5 | 5 |
| 11 | Barium sulfate | 10 | 10 | 10 |
| 12 | Mica titanium | 3 | 3 | 3 |

Preparation Method

Step A: Components 8 to 12 were dispersed homogeneously.

Step B: Components 1 to 7 were mixed homogeneously, added to A, and made homogeneous.

Step C: The mixture was placed in a container and press molded to obtain a foundation.

The powder foundations thus obtained were stored at a temperature of 45 degrees C. for one month, and then the change in appearance was observed visually. The foundations of Examples 112 and 113 did not exhibit any change in appearance but the foundation of Comparative Example 13 cracked. It was also recognized that the powder partly agglomerated when it was taken with a puff. Thus, it was found that formulation of a resin having a reactive group lowers storage stability.

Examples 114 to 116

10 g of the copolymer from Preparation Example 8 was dissolved in 50 g of decamethylcyclopentasiloxane and 40 g of titanium oxide (MT-100TV, from Tayca Corporation) was added. The mixture was dispersed with a beads mill to obtain a dispersion of titanium oxide (A).

Separately, 8 g of the copolymer from Preparation Examples 22 was dissolved in 42 g of decamethylcyclopentasiloxane and 50 g of zinc oxide (MZ505S, from Tayca Corporation) was added. The mixture was dispersed with a beads mill to obtain a dispersion of zinc oxide (B).

Using each dispersion described above, sunscreen agents were prepared according to the prescription indicated in the Table below.

TABLE 50

| Component | Ingredient | Ex. 114 | Ex. 115 | Ex. 116 |
|---|---|---|---|---|
| 1 | Dimethylpolysiloxane (viscosity 6 mm$^2$/s) | 5 | 5 | 5 |
| 2 | KSG-210*[5] | 5 | 5 | 5 |
| 3 | Glyceryl trioctanoate | 3 | 3 | 3 |
| 4 | KF-6019*[35] | 1 | 1 | 1 |
| 5 | Octyl paramethoxycinnamate | 6 | 6 | 6 |
| 6 | Sodium chloride | 0.5 | 0.5 | 0.5 |
| 7 | 1,3-Butylene glycol | 2 | 2 | 2 |
| 8 | Purified water | Balance | Balance | Balance |
| 9 | Decamethylcyclopentasiloxane | 20 | 20 | 20 |
| 10 | Titanium oxide dispersion (A) | 20 | 0 | 10 |
| 11 | Zinc oxide dispersion (B) | 0 | 20 | 10 |

Preparation Method

Step A: Components 1 to 5 and Components 9 to 11 were dispersed homogeneously.

Step B: Components 6 to 8 were dissolved.

Step C: B was added to A and emulsified.

The sunscreen agents thus obtained were non-greasy, non-sticky, and refreshing, and provided a good adhesive feel.

The silicone products used in the above Examples are as follows:

| | Trade name | Manufacturer | Chemical name (INCI name) |
|---|---|---|---|
| *1 | KSG15 | Shin-Etsu Chemical Co., Ltd. | Cross-linked silicone composition (Cyclomethicone; Dimethicone/Vinyl Dimethicone Crosspolymer) |
| *2 | KSG16 | Shin-Etsu Chemical Co., Ltd. | Cross-linked silicone composition (Dimethicone; Dimethicone/Vinyl Dimethicone Crosspolymer) |
| *3 | KSG18 | Shin-Etsu Chemical Co., Ltd. | Cross-linked silicone composition (Phenyl Trimethicone; Dimethicone/Phenyl Vinyl Dimethicone Crosspolymer) |
| *4 | KSG21 | Shin-Etsu Chemical Co., Ltd. | Cross-linked polyether-modified silicone composition (Dimethicone; Dimethicone PEG-10 Crosspolymer) |
| *5 | KSG210 | Shin-Etsu Chemical Co., Ltd. | Cross-linked polyether-modified silicone composition (Dimethicone; Dimethicone PEG-10/15 Crosspolymer) |
| *6 | KSG41 | Shin-Etsu Chemical Co., Ltd. | Cross-linked alkyl-modified silicone composition (Mineral Oil; Vinyl Dimethicone/Lauryl Dimethicone Crosspolymer) |
| *7 | KSG42 | Shin-Etsu Chemical Co., Ltd. | Cross-linked alkyl-modified silicone composition (Isododecane; Vinyl Dimethicone/Lauryl Dimethicone Crosspolymer) |
| *8 | KSG43 | Shin-Etsu Chemical Co., Ltd. | Cross-linked alkyl-modified silicone composition (Triethylhexanoin; Vinyl Dimethicone/Lauryl Dimethicone Crosspolymer) |
| *9 | KSG44 | Shin-Etsu Chemical Co., Ltd. | Cross-linked alkyl-modified silicone composition (Squalan; Vinyl Dimethicone/Lauryl Dimethicone Crosspolymer) |
| *10 | KSG310 | Shin-Etsu Chemical Co., Ltd. | Cross-linked alkylpolyether-modified silicone composition (Mineral Oil; PEG-15/Lauryl Dimethicone Crosspolymer) |
| *11 | KSG320 | Shin-Etsu Chemical Co., Ltd. | Cross-linked alkylpolyether-modified silicone composition (Isododecane; PEG-15/Lauryl Dimethicone Crosspolymer) |
| *12 | KSG330 | Shin-Etsu Chemical Co., Ltd. | Cross-linked alkylpolyether-modified silicone composition (Triethylhexanoin; PEG-15/Lauryl Dimethicone Crosspolymer) |
| *13 | KSG340 | Shin-Etsu Chemical Co., Ltd. | Cross-linked alkylpolyether-modified silicone composition (Squalan; PEG-10/Lauryl Dimethicone Crosspolymer; PEG-15/Lauryl Dimethicone Crosspolymer) |
| *14 | KSG710 | Shin-Etsu Chemical Co., Ltd. | Cross-linked polyglycerin-modified silicone composition |
| *15 | KSG810 | Shin-Etsu Chemical Co., Ltd. | Cross-linked alkylpolyglycerin-modified silicone composition |
| *16 | KSG820 | Shin-Etsu Chemical Co., Ltd. | Cross-linked alkylpolyglycerin-modified silicone composition |
| *17 | KSG830 | Shin-Etsu Chemical Co., Ltd. | Cross-linked alkylpolyglycerin-modified silicone composition |
| *18 | KSG840 | Shin-Etsu Chemical Co., Ltd. | Cross-linked alkylpolyglycerin-modified silicone composition |

-continued

| | Trade name | Manufacturer | Chemical name (INCI name) |
|---|---|---|---|
| *19 | KP541 | Shin-Etsu Chemical Co., Ltd. | Acryl/silicone graft copolymer (Isopropyl Alcohol; Acrylates/Dimethicone Copolymer) |
| *20 | KP545 | Shin-Etsu Chemical Co., Ltd. | Acryl/silicone graft copolymer (Cyclopentasiloxane; Acrylates/Dimethicone Copolymer) |
| *21 | KP561P | Shin-Etsu Chemical Co., Ltd. | Acryl/silicone graft copolymer (Acrylates/Stearyl Acrylate/Dimethicone Methacrylate Copolymer) |
| *22 | KP562P | Shin-Etsu Chemical Co., Ltd. | Acryl/silicone graft copolymer (Acrylates/Behenyl Acrylate/Dimethicone Methacrylate Copolymer) |
| *23 | KP575 | Shin-Etsu Chemical Co., Ltd. | Acryl/silicone graft copolymer/decamethylcyclopentasiloxane solution |
| *24 | KSP100 | Shin-Etsu Chemical Co., Ltd. | Spherical silicone powder (Vinyl Dimethicone/Methicone Silsesquioxane Crosspolymer) |
| *25 | KSP101 | Shin-Etsu Chemical Co., Ltd. | Spherical silicone powder (Vinyl Dimethicone/Methicone Silsesquioxane Crosspolymer) |
| *26 | KSP200 | Shin-Etsu Chemical Co., Ltd. | Spherical silicone powder (Trfluoropropyl Dimethicone/Vinyl Trifluoropropyl Dimethicone/Silsesquioxane Crosspolymer) |
| *27 | KSP300 | Shin-Etsu Chemical Co., Ltd. | Spherical silicone powder (Diphenyl Dimethicone/Vinyl Diphenyl Dimethicone/Silsesquioxane Crosspolymer) |
| *28 | KMP590 | Shin-Etsu Chemical Co., Ltd. | Spherical silicone powder(Polymethylsilsesquioxane) |
| *29 | KF7312J | Shin-Etsu Chemical Co., Ltd. | Trimethylsiloxy silicate/decamethylcyclopentasiloxane solution (Trimethylsiloxysilicate; Cyclopentasiloxane) |
| *30 | KF6009 | Shin-Etsu Chemical Co., Ltd. | Polyeter-modified silicone at both ends (PEG-9 Dimethicone) |
| *31 | KF6011 | Shin-Etsu Chemical Co., Ltd. | Polyether-modified silicone(PEG-11 Methyl Ether Dimethicone) |
| *32 | KF6015 | Shin-Etsu Chemical Co., Ltd. | Polyether-modified silicone(PEG-3 Dimethicone) |
| *33 | KF6017 | Shin-Etsu Chemical Co., Ltd. | Polyether-modified silicone(PEG-10 Dimethicone) |
| *34 | KF6018 | Shin-Etsu Chemical Co., Ltd. | Polyether-modified silicone(PEG-11 Methyl Ether Dimethicone) |
| *35 | KF6019 | Shin-Etsu Chemical Co., Ltd. | Polyether-modified silicone(PEG-9 Dimethicone) |
| *36 | KF6026 | Shin-Etsu Chemical Co., Ltd. | Oleylpolyether-modified silicone(PEG/PPG-10/3 Oleyl Ether Dimethicone) |
| *37 | KF6028 | Shin-Etsu Chemical Co., Ltd. | Silicone graft polyether-modified silicone(PEG-9 Polydimethylsiloxyethyl Dimethicone) |
| *38 | KF6100 | Shin-Etsu Chemical Co., Ltd. | Polyglycerin-modified silicone |
| *39 | KF6104 | Shin-Etsu Chemical Co., Ltd. | Polyglycerin-modified silicone |
| *40 | KF6105 | Shin-Etsu Chemical Co., Ltd. | Alkylpolyglycerin-modified silicone (Lauryl Polyglyceryl-3 Polydimethylsiloxyethyl Dimethicone) |
| *41 | SPD-T5 | Shin-Etsu Chemical Co., Ltd. | Titanium oxide/decamethylcyclopentasiloxane dispersion |
| *42 | SPD-Z5 | Shin-Etsu Chemical Co., Ltd. | Zinc oxide/decamethylcyclopentasiloxane dispersion |
| *43 | SPD-T1S | Shin-Etsu Chemical Co., Ltd. | Titanium oxide/decamethylcyclopentasiloxane dispersion (Cyclopentasiloxan; Titanium Dioxide; Alumina; Stearic Acid; Acrylates/Ethylhexyl Acrylate/Dimethicone Methacrylate Copolymer) |
| *44 | SPD-Z1S | Shin-Etsu Chemical Co., Ltd. | Zinc oxide/decamethylcyclopentasiloxane dispersion (Zinc Oxide; Cyclopentasiloxane; Acrylates/Ethylhexyl Acrylate/Dimethicone Methacrylate Copolymer; Triethoxysilylethyl Polydimethylsiloxyethyl Hexyl Dimethicone) |
| *45 | KF56 | Shin-Etsu Chemical Co., Ltd. | Methylphenylsilicone(Phenyl Trimethicone) |
| *46 | Metholose 65-SH4000 | Shin-Etsu Chemical Co., Ltd. | Methyl cellulose |
| *47 | Metholose SM400 | Shin-Etsu Chemical Co., Ltd. | Methyl cellulose |
| *48 | Rheoperal TT | Chiba Seifun | Dextrin ester of aliphatic acid |
| *49 | Rheoperal ISK | Chiba Seifun | Fructo-oligo saccharide stearate |
| *50 | Spigel305 | SEPIC | Emulsifier of polyacrylamide type |
| *51 | Aristoflex AVC | Clariant | Water-soluble polymer |
| *52 | Bentone 38 | NL Industries Inc. | Organically modified clay minerals |
| *53 | FL-5 | Shin-Etsu Chemical Co., Ltd. | Fluorine-modified silicone(Trifluoropropyl Dimethicone) |
| *54 | FPD6131 | Shin-Etsu Chemical Co., Ltd. | Fluorinated polyether-modified silicone(PEG-8 Trifluoropropyl Dimethicone Copolymer) |
| *55 | KF9909 | Shin-Etsu Chemical Co., Ltd. | Silicone graft reactive hexyl modified silicone (Triethoxysilylethyl Polydimethylsiloxyethyl Hexyl Dimethicone) |
| *56 | Aerosil R972 | Nippon Aerosil Co. | Silica treated for hydrophobicity |
| *57 | Aerosil RY200 | Nippon Aerosil Co. | Silica treated for hydrophobicity |

| Trade name | Manufacturer | Chemical name (INCI name) |
|---|---|---|
| *58 KF7002 | Shin-Etsu Chemical Co., Ltd. | Stearoxy modified silicone |
| *59 Titanium TTO-S2 | Sakai Chemical Industry Co., Ltd. | Fine particle titanium oxide treated for hydrophobicity |
| *60 Sunsphere SZ-5 | Asahi Glass Co., Ltd. | Anhydrous silicic acid treated zinc oxide |

INDUSTRIAL APPLICABILITY

The cosmetic thus obtained extended lightly and gave refreshing feel to the skin without stickiness, because of the polymer having properties of both silicone and phophoryl moieties. The applied cosmetic adhered well to the skin and was durable. The cosmetics do not irritate the skin and is stable with time, because the polymer does not have reactive groups such as an alkoxyl group.

The invention claimed is:

1. A cosmetic comprising (A) a polymer having repeating units represented by the following formulas (I) and (II):

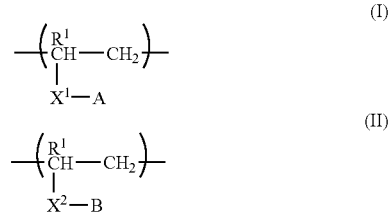

wherein each $R^1$ may be the same with or different from each other and is a hydrogen atom or a methyl group,
each of $X^1$ and $X^2$ has 2 to 10 carbon atoms and is a divalent aromatic group or a group represented by the formula, $—COOR^7—$, wherein $R^7$ is an aliphatic group bonded to A or B,
A is an organopolysiloxane residue, and
B is a group represented by the following formula (1),

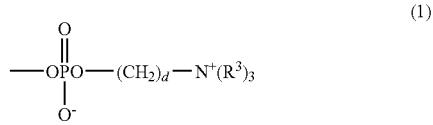

wherein each $R^3$ may be the same or different from each other and is an alkyl group having 1 to 20 carbon atoms and d is an integer of from 1 to 10, and (B) an unctuous agent.

2. The cosmetic according to claim 1, wherein, in the repeating unit represented by the formula (I), $X^1$ is represented by the formula, $—COO(CH_2)_a—$, wherein a is an integer of from 1 to 9, or a phenylene group, and the organopolysiloxane residue A is represented by the following formula (2),

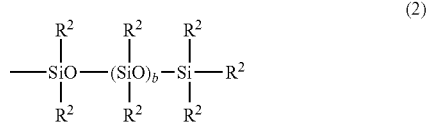

wherein b is an integer of from 1 to 300, and $R^2$ may be the same with or different from each other and is a $C_{1-30}$ alkyl or an aryl group, which is fluorinated or not substituted.

3. The cosmetic according to claim 1, wherein, in the repeating unit represented by the formula (II), $X^2$ is represented by the formula, $—COO(CH_2)_c—$, wherein c is an integer of from 1 to 10, and $R^3$ is a methyl group.

4. The cosmetic according to claim 1, wherein the polymer further has repeating units (III) derived from at least one radically polymeraizable monomer selected from the group consisting of unsaturated carboxylic acids and derivatives thereof, vinylpyrrolidone and derivatives thereof and styrene and derivatives thereof.

5. The cosmetic according to claim 4, wherein the repeating unit (III) is derived from at least one selected from the group consisting of (meth)acylic acid, (meth)acrylates, (meth)acrylamides and vinylpyrrolidone.

6. The cosmetic according to claim 5, wherein the (meth)acrylate is polyoxyalkylene mono(meth)acrylate, or (poly) glycerin mono(meth)acrylate.

7. The cosmetic according to claim 6, wherein the polyoxyalkylene mono(meth)acrylate is represented by the following formula (3),

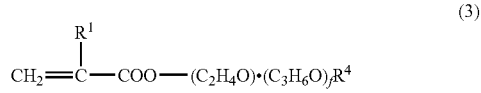

wherein $R^1$ is a hydrogen atom or a methyl group, $R^4$ is a hydrogen atom, a $C_{1-30}$ alkyl or acetyl group, and each of e and f is an integer of from 0 to 100 with a sum of e and f ranging from 5 to 200.

8. The cosmetic according to claim 6, wherein the (poly) glycerin mono(meth)acrylate is represented by the following formula (4),

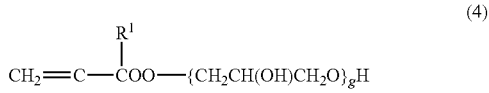

wherein $R^1$ is a hydrogen atom or a methyl group, and g is an integer ranging from 1 to 3.

9. The cosmetic according to claim 1, wherein the polymer comprises 1.0 to 29.0 mass % of the repeating unit (I) and 71.0 to 99.0 mass % of the repeating unit (II), based on a mass of the polymer.

10. The cosmetic according to claim 1, wherein the polymer comprises 30.0 to 99.5 mass % of the repeating unit (I) and 0.5 to 70.0 mass % of the repeating unit (II), based on a mass of the polymer.

11. The cosmetic according to claim 4, wherein the polymer comprises 1.0 to 29.0 mass % of the repeating unit (I), 0.5 to 69.5 mass % of the repeating unit (II), and 29.5 to 98.5 mass % of the repeating unit (III), based on a mass of the polymer (A).

12. The cosmetic according to claim 4, wherein the polymer comprises 30.0 to 99.0 mass % of the repeating unit (I), 0.5 to 69.5 mass % of the repeating unit (II), and 0.5 to 69.5 mass % of the repeating unit (III), based on a mass of the polymer (A).

13. The cosmetic according to claim 1, wherein at least a part of said unctuous agent (B) is liquid at room temperature.

14. The cosmetic according to claim 1, wherein at least a part of said unctuous agent (B) is a silicone oil.

15. The cosmetic according to claim 14, wherein at least a part of said unctuous agent (B) is at least one selected from the group consisting of a linear silicone oil represented by the following formula (8), a cyclic silicone oil represented by the following formula (9) and a branched silicone oil represented by the following formula (10):

$$(CH_3)_j R^5_{3-j} SiO(SiO)_h(SiO)_i Si(CH_3)_k \text{ with } CH_3, R^5, R^5_{3-k}, CH_3, CH_3 \text{ substituents} \tag{8}$$

$$[(SiO)_l(SiO)_m] \text{ with } CH_3, R^5, CH_3, CH_3 \text{ substituents} \tag{9}$$

$$R^6_{4-n}Si\{OSi(CH_3)_3\}_n \tag{10}$$

wherein $R^5$ may be the same with or different from each other and is selected from the group consisting of a hydrogen atom, a hydroxyl group, $C_{2-20}$ alkyl groups which may be fluorinated or aminated, $C_{6-20}$ arly groups, $C_{6-22}$ alkoxy groups, and the groups represented by the formula, $(CH_3)_3SiO\{(CH_3)_2SiO\}_p Si(CH_3)_2CH_2CH_2$—, wherein p is an integer of from 0 to 500;

$R^6$ is a $C_{1-20}$ alkyl group, each of h and i is an integer ranging from 0 to 1000 with a sum of h and i ranging from 1 to 2000, each of j and k is an integer of from 0 to 3, each of l and m is an integer of from 0 to 8 with a sum of l and m ranging from 3 to 8 and n is an integer of from 1 to 4.

16. The cosmetic according to claim 15, wherein at least a part of said unctuous agent (B) is at least one selected from the group consisting of the linear silicone oil represented by the formula (8) with a part of $R^5$ being an aminated or fluorinated $C_{2-20}$ alkyl group, the cyclic silicone oil represented by the formula (9) with a part of $R^5$ being an aminated or fluorinated $C_{2-20}$ alkyl group, a cyclic organopolysiloxane composed of repeating units represented by the formula, —$\{(CF_3CH_2CH_2)(CH_3)SiO\}_q$—, wherein q is an integer of from 3 to 8, perfluoropolyether, perfluorodecalin, and perfluoroctane.

17. The cosmetic according to claim 1, wherein the cosmetic further comprises (C) a $C_{2-10}$ compound having an alcoholic hydroxyl group.

18. The cosmetic according to claim 1, wherein the cosmetic further comprises (D) a water-soluble polymer and/or water-swellable polymer.

19. The cosmetic according to claim 1, wherein the cosmetic further comprises (E) water.

20. The cosmetic according to claim 1, wherein the cosmetic further comprises (F) powder.

21. The cosmetic according to claim 20, wherein at least a part of said powder is at least one selected from the group consisting of silicone elastomer spherical powder, polymethylsilsesquioxane spherical powder, silicone elastomer spherical powder coated with polymethylsilsesquioxane, polyethylene powder, polypropylene powder, polytetrafluoroethylene powder, and polyurethane powder.

22. The cosmetic according to claim 1, wherein the cosmetic further comprises (G) a surfactant.

23. The cosmetic according to claim 22, wherein the surfactant (G) is a silicone having a polyoxyalkylene chain or polyglycerin chain in a molecule.

24. The cosmetic according to claim 23, wherein the surfactant (G) has 5 to 50 mass %, based on a molecular weight of the surfactant (G), of the polyoxyalkylene chain or the polyglycerin chain.

25. The cosmetic according to claim 1, wherein the cosmetic further comprises (H) a crosslinked organopolysiloxane.

26. The cosmetic according to claim 25, wherein the crosslinked organopolysiloxane (H) is swelled with the unctuous agent (B) having a viscosity of from 0.65 mm$^2$/sec to 100.0 mm$^2$/sec.

27. The cosmetic according to claim 25, wherein the crosslinked organopolysiloxane (H) has a crosslinkage formed by a reaction of a crosslinking agent having at least two reactive vinylic groups with a hydrogen atom bonded directly to a silicon atom.

28. The cosmetic according to claim 25, wherein the crosslinkage in the crosslinked organopolysiloxane (H) has at least one moiety selected from the group consisting of polyoxyalkylene, alkyl, alkenyl, aryl, fluoroalkyl and polygrycerin moieties.

29. The cosmetic according to claim 1, wherein the cosmetic further comprises (I) a silicone resin which is gummy or solid at 25° C. and homogeneously soluble in decamethylcyclopentasiloxane.

30. The cosmetic according to claim 29, wherein the silicone resin (I) is a silicone compound having a network structure, expressed by MQ, MT, MDQ, MDT, MTQ, MDTQ, TD, TQ, or TDQ.

31. The cosmetic according to claim 30, wherein the silicone resin (I) has at least one moiety selected from the group consisting of pyrrolidone, long-chain alkyl, polyoxyalkylene, fluoroalkyl, and amino moieties.

32. The cosmetic according to claim 1, wherein the cosmetic further comprises (J) an acrylic silicone resin except the silicone polymer (A).

33. The cosmetic according to claim 1, wherein the cosmetic further comprises (K) a UV-ray protective agent.

34. The cosmetic according to claim 1, wherein the cosmetic is a skin care cosmetic, a hair care cosmetic, an antiperspirant, a makeup cosmetic, or a UV-ray protective cosmetic.

35. The cosmetic according to claim 1, wherein the cosmetic is in the form of liquid, emulsion, cream, solid, paste, gel, powder, pressed form, multi-layered form, mousse, spray, or stick.

* * * * *